(12) United States Patent
Aikins et al.

(10) Patent No.: US 7,316,687 B2
(45) Date of Patent: Jan. 8, 2008

(54) BLADE PLATE AND INSTRUMENTS

(75) Inventors: Jerry L. Aikins, Warsaw, IN (US); George Brian Cornwall, San Diego, CA (US); Raymond Desjardins, Ontario (CA); Paul Duwelius, Lake Oswego, OR (US); James Goulet, Ann Arbor, MI (US); David Templeman, Plymouth, MN (US); John E. Meyers, Columbia City, IN (US); Scott A. Moon, Valparaiso, IN (US); Gregory G. Price, Warsaw, IN (US); Patrick Rousseau, Hardwick, NJ (US); Roy Wiley, Warsaw, IN (US); Robert A. Winquist, Seattle, WA (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

(21) Appl. No.: 09/939,412

(22) Filed: Aug. 24, 2001

(65) Prior Publication Data

US 2003/0040748 A1   Feb. 27, 2003

(51) Int. Cl.
*A61B 17/58* (2006.01)
(52) U.S. Cl. .......................... 606/70; 606/69
(58) Field of Classification Search ............ 606/60, 606/69–73, 86, 96, 105, 67, 66, 65; 248/248
See application file for complete search history.

(56) References Cited

U.S. PATENT DOCUMENTS 2,500,993 A * 3/1950 Mason ........................ 606/67
2,716,406 A * 8/1955 Reymann et al. ............. 606/67

(Continued)

FOREIGN PATENT DOCUMENTS

DE        3722-852        1/1989

(Continued)

OTHER PUBLICATIONS

"The Closed Wedge Varus Supracondylar Osteotomy", Rene K. Martin, M.D., et al.; The Department of Orthopaedic Srugery, Amsterdam, The Netherlands; 2000, pp. 48-55.

(Continued)

*Primary Examiner*—Eduardo C. Robert
*Assistant Examiner*—James L Swiger
(74) *Attorney, Agent, or Firm*—Baker & Daniels LLP

(57) ABSTRACT

A blade plate, as well as instruments and methods for securing the blade plate to a bone to reduce a bone fracture. The blade plate includes a plate portion and a blade portion extending at an angle relative to the plate portion. The plate portion includes a plurality of holes for receipt of bone screws for securing the blade plate to the bone about the bone fracture. A strut screw, inserted through a hole in the plate portion, spans the angle between the plate and blade portions, and threadingly engages a hole in the blade portion to slightly draw the plate and blade portions together to compress and support the bone fracture. A pair of top screws are inserted through holes in the plate portion at angles with respect to the strut screw on either side of the strut screw. Additionally, the blade plate is designed to closely conform to the surface of the bone to minimize the gap between the bone and the blade plate. In order to secure the blade plate to a bone, a chisel/drill guide, chisel, insertion guide, and screw drill guides are provided.

13 Claims, 17 Drawing Sheets

U.S. PATENT DOCUMENTS

| | | | |
|---|---|---|---|
| 3,593,709 A | * | 7/1971 | Halloran ..................... 606/69 |
| 3,716,050 A | * | 2/1973 | Johnston ..................... 606/69 |
| 3,824,995 A | * | 7/1974 | Getscher et al. ............. 606/69 |
| 4,565,193 A | * | 1/1986 | Streli ........................ 606/69 |
| 4,823,780 A | * | 4/1989 | Odensten et al. ............ 606/96 |
| 4,936,844 A | * | 6/1990 | Chandler et al. ............ 606/69 |
| 5,006,120 A | * | 4/1991 | Carter ....................... 606/69 |
| 5,087,260 A | | 2/1992 | Fixel |
| 5,190,544 A | * | 3/1993 | Chapman et al. ............ 606/69 |
| 5,290,312 A | * | 3/1994 | Kojimoto et al. ........ 623/17.15 |
| 5,300,074 A | * | 4/1994 | Frigg ........................ 606/67 |
| 5,364,399 A | * | 11/1994 | Lowery et al. .............. 606/69 |
| 5,365,996 A | * | 11/1994 | Crook ....................... 164/45 |
| 5,429,641 A | * | 7/1995 | Gotfried ..................... 606/67 |
| 5,662,655 A | * | 9/1997 | Laboureau et al. .......... 606/75 |
| 5,674,222 A | * | 10/1997 | Berger et al. ............... 606/69 |
| 5,749,872 A | * | 5/1998 | Kyle et al. .................. 606/69 |
| 6,183,475 B1 | | 2/2001 | Lester et al. |
| 6,283,969 B1 | * | 9/2001 | Grusin et al. ............... 606/69 |
| 2003/0060827 A1 | * | 3/2003 | Coughin ..................... 606/70 |

OTHER PUBLICATIONS

2411-"Condylar Blade-Plates With SCP Hole", p. C39 of Zimmer catalog; 1987.

Pages 19, 20 & 21 from a Medical Device Catalog.

Section 3.7 of Manual of Internal Fixation, 8th Edition, 1991, pp. 252-269.

SYNTHES® 4.5mm 90° Cannulated LC-Angled Blade Plates, Stainless Steel and Titanium Technique Guide, 1998.

* cited by examiner

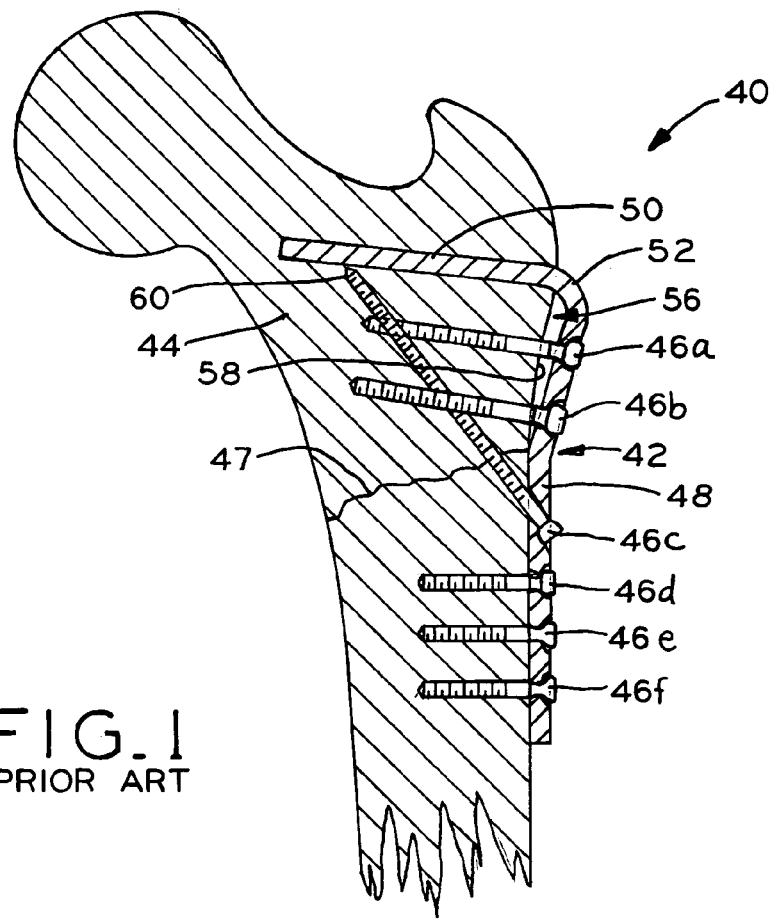
FIG_1
PRIOR ART
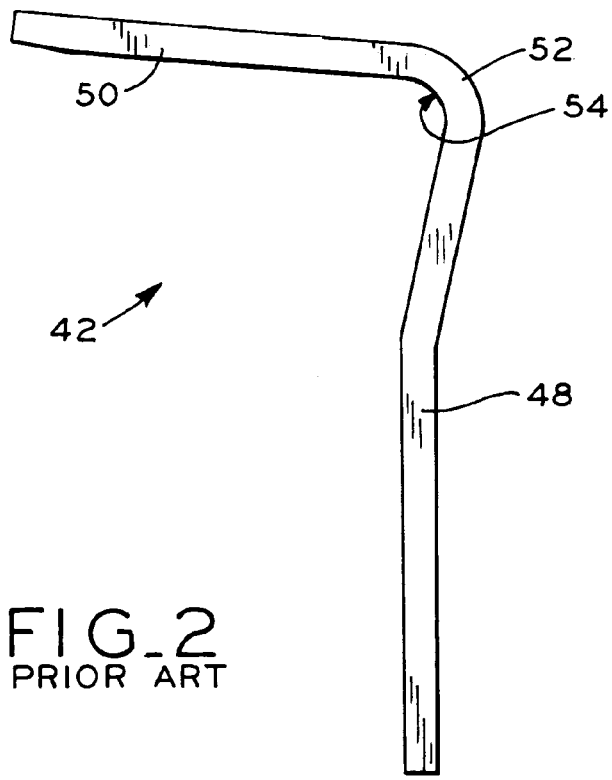
FIG_2
PRIOR ART

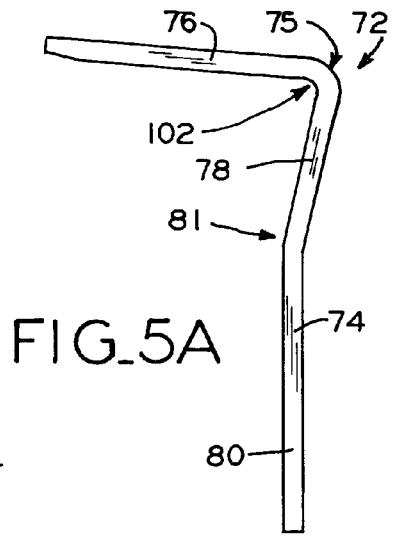
FIG_5A
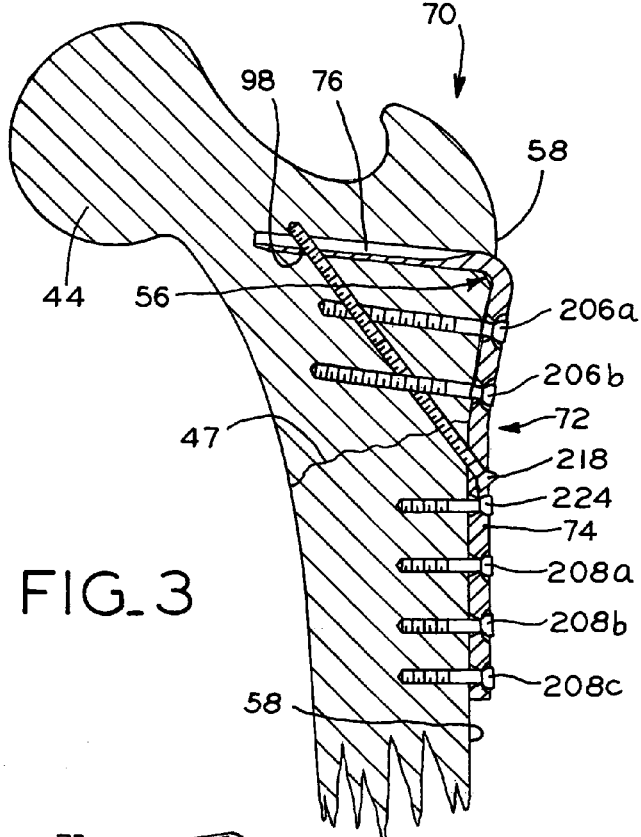
FIG_3
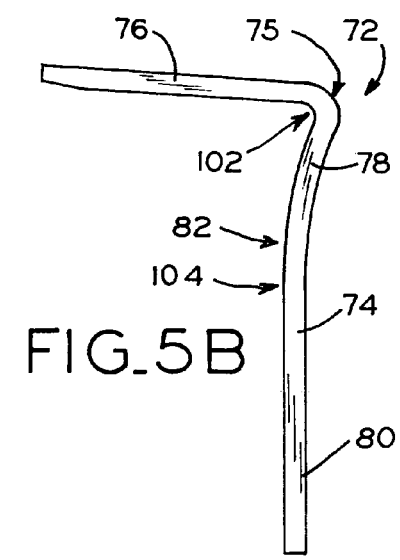
FIG_5B
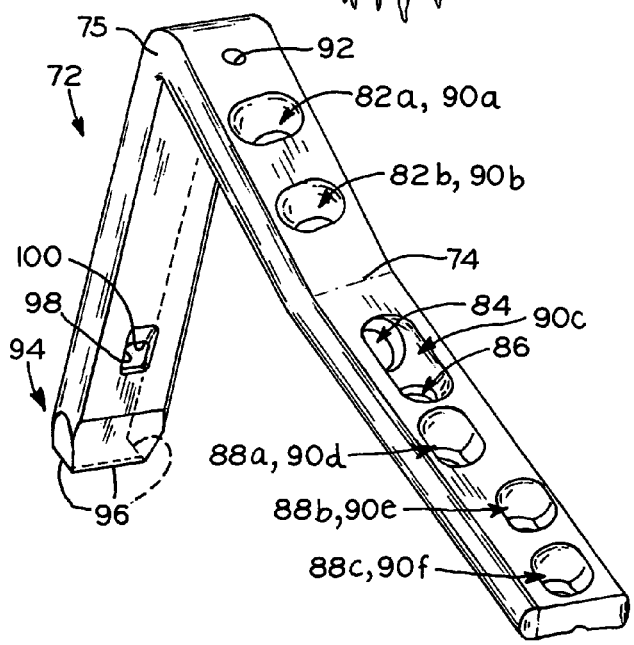
FIG_4

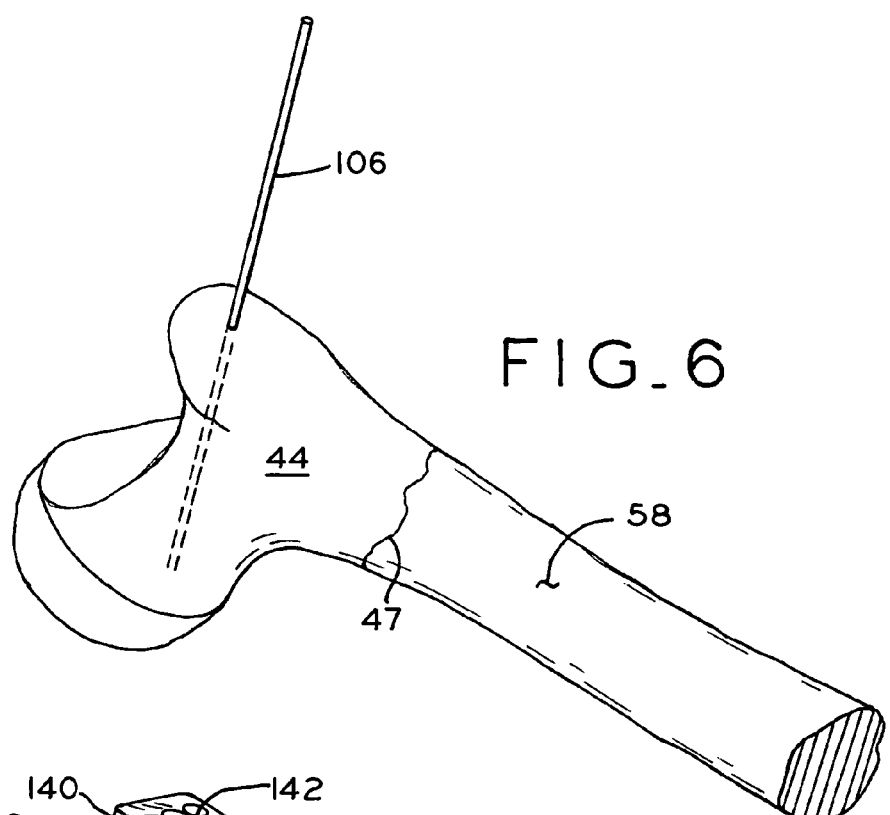
FIG_6
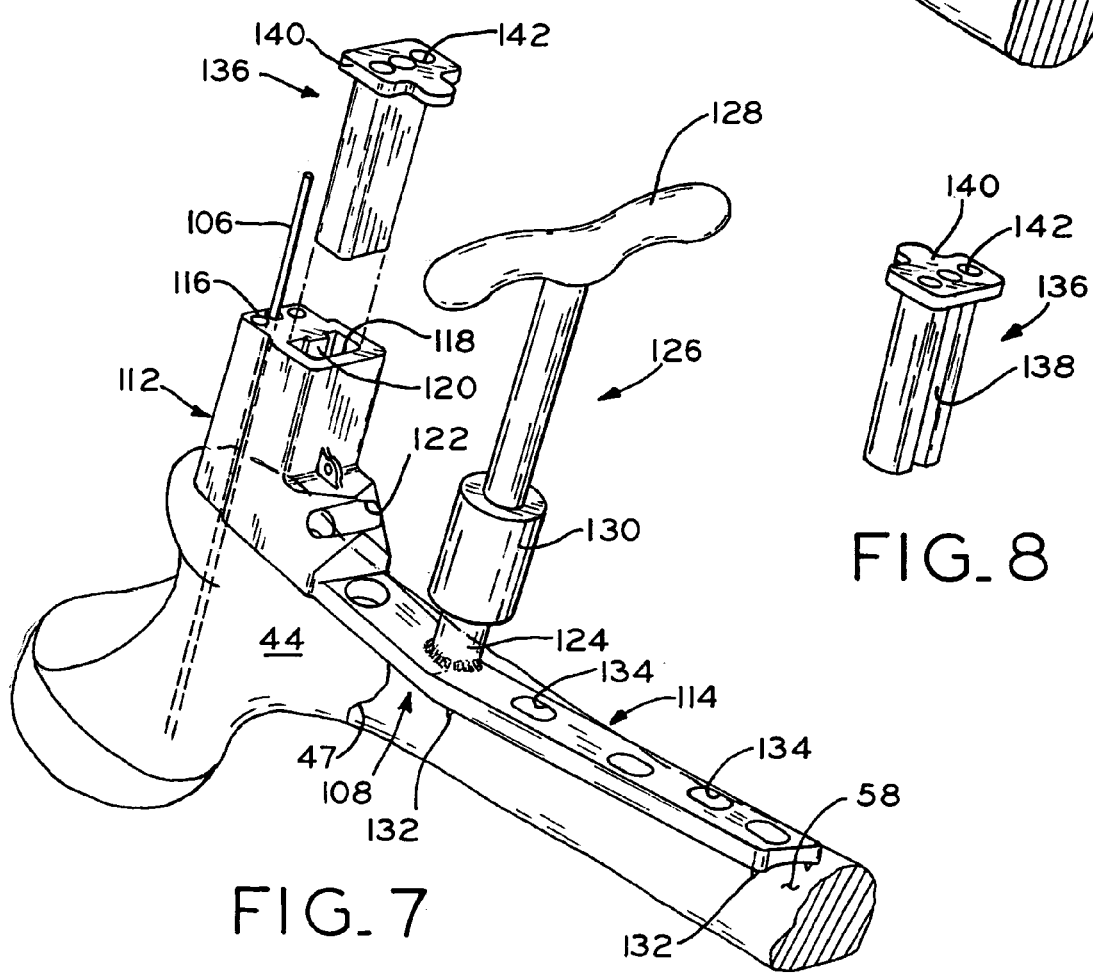
FIG_7
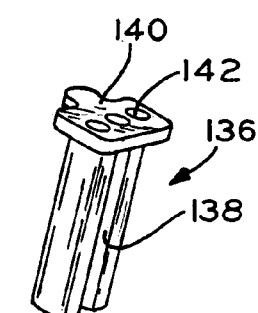
FIG_8

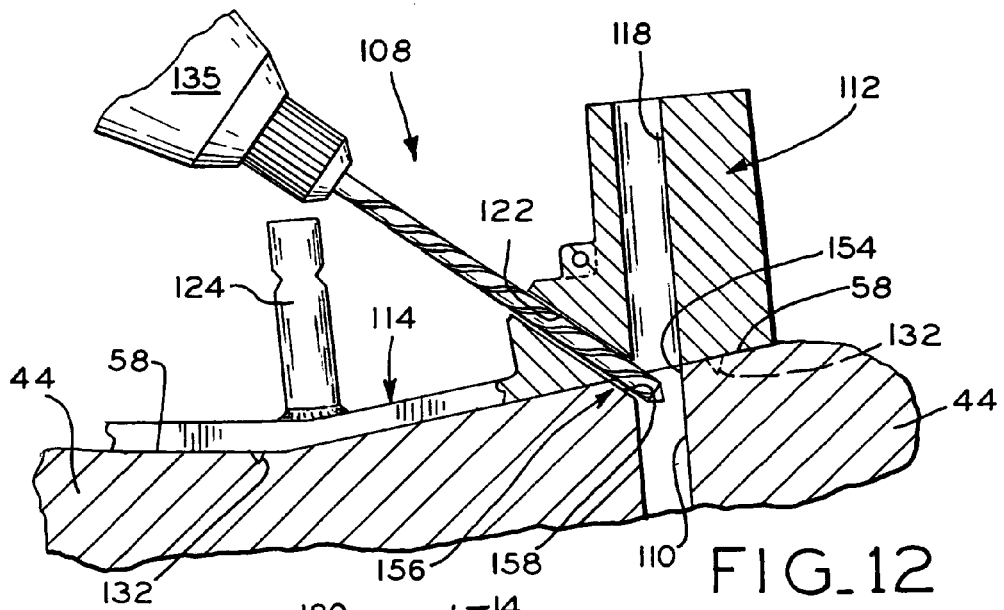
FIG_12
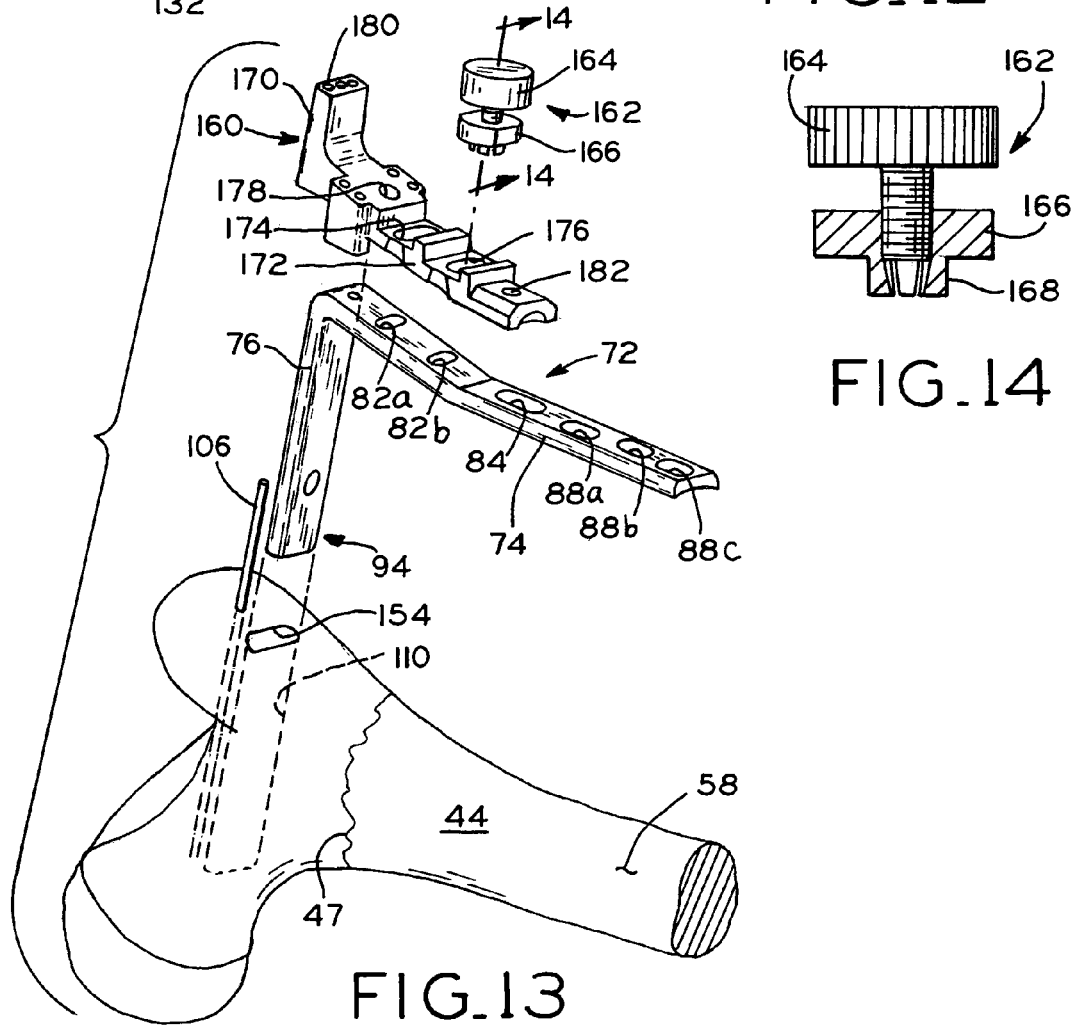
FIG_14
FIG_13

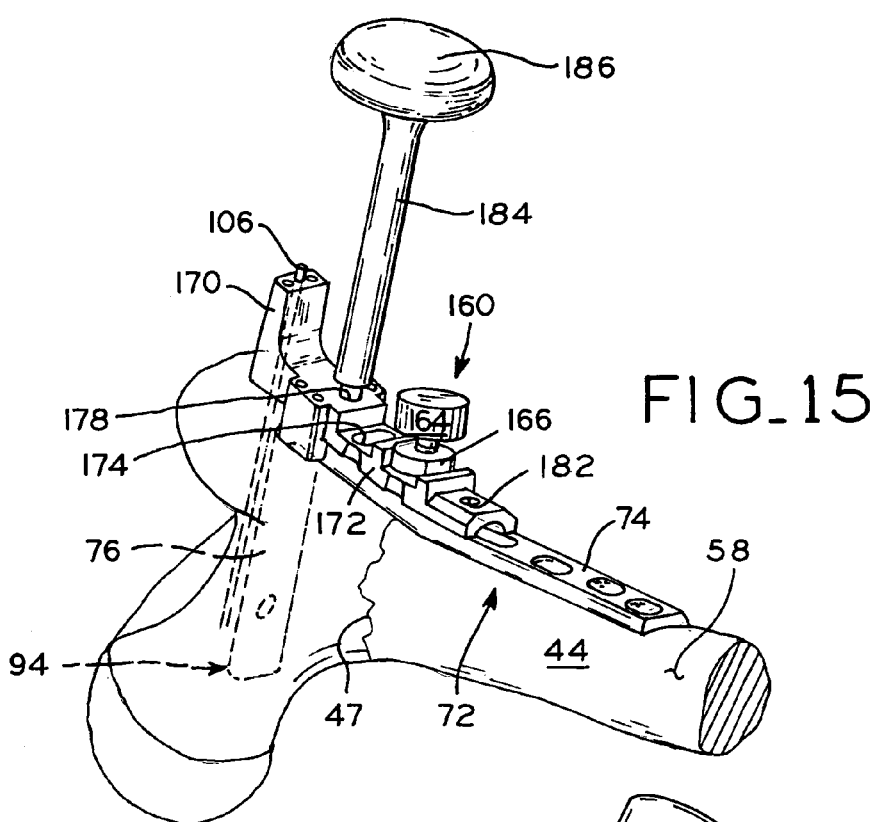
FIG_15
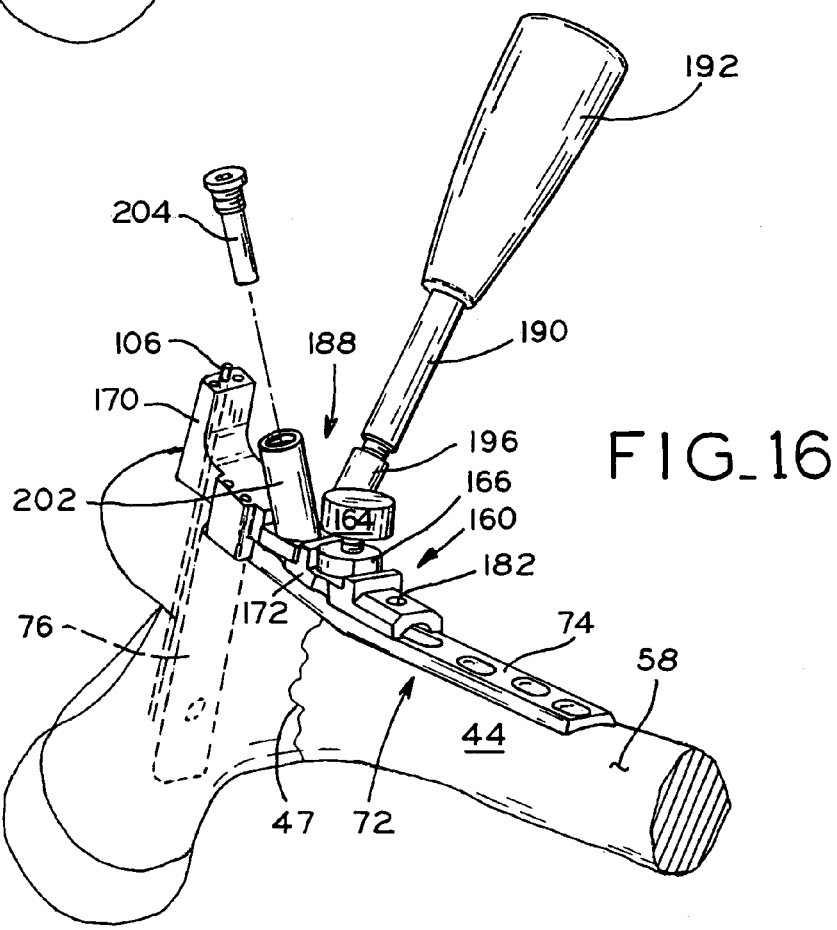
FIG_16

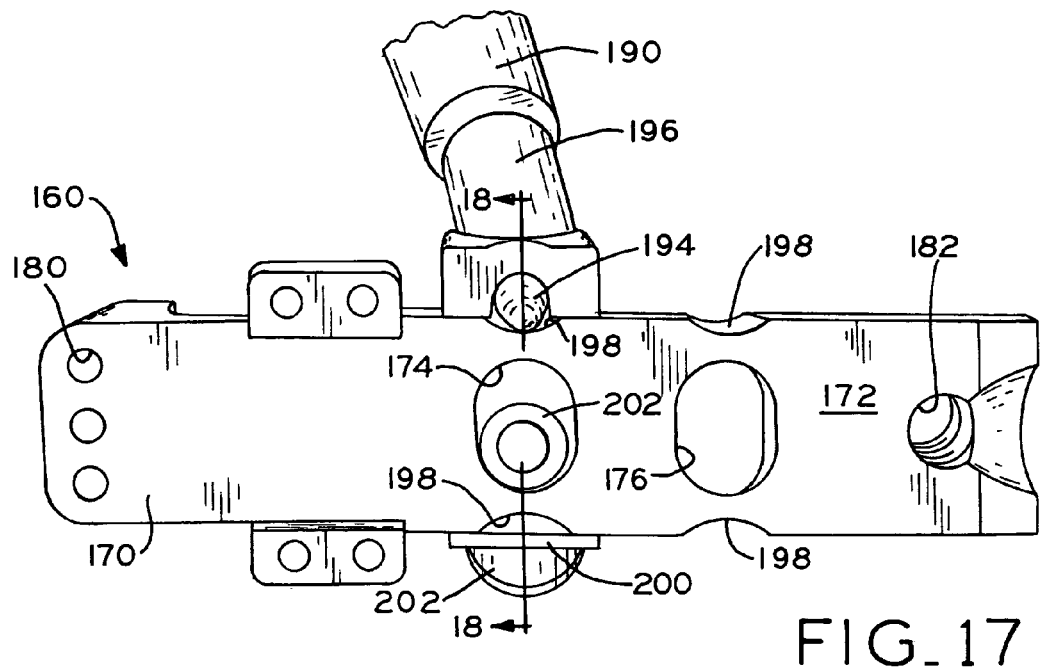
FIG_17
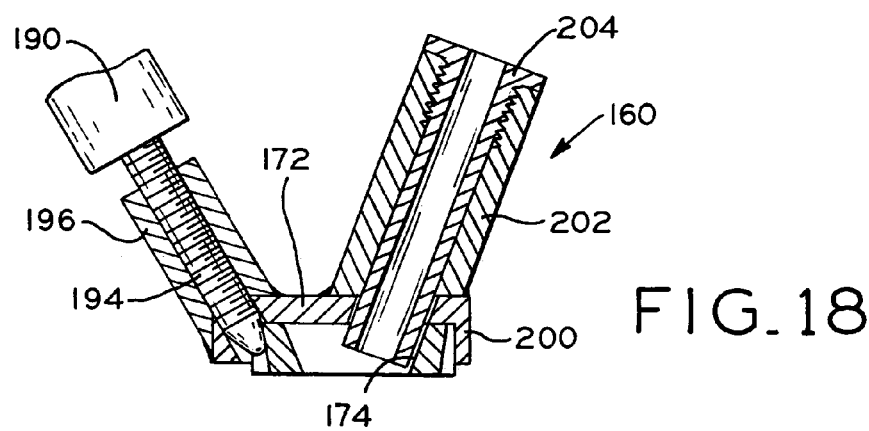
FIG_18

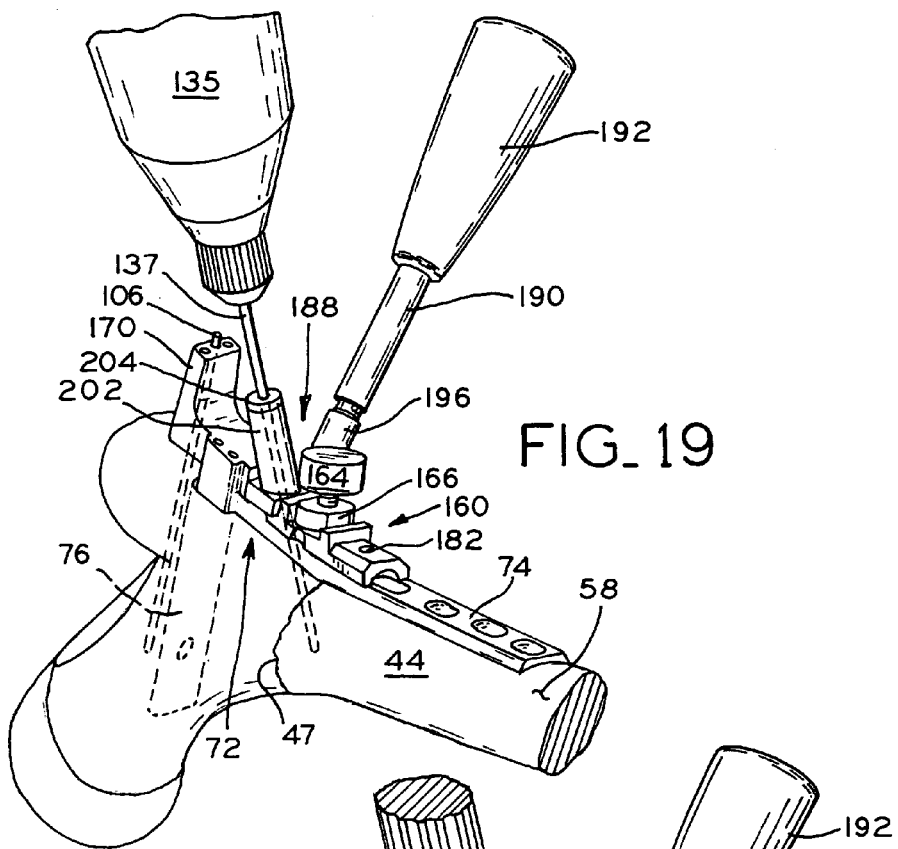
FIG_19
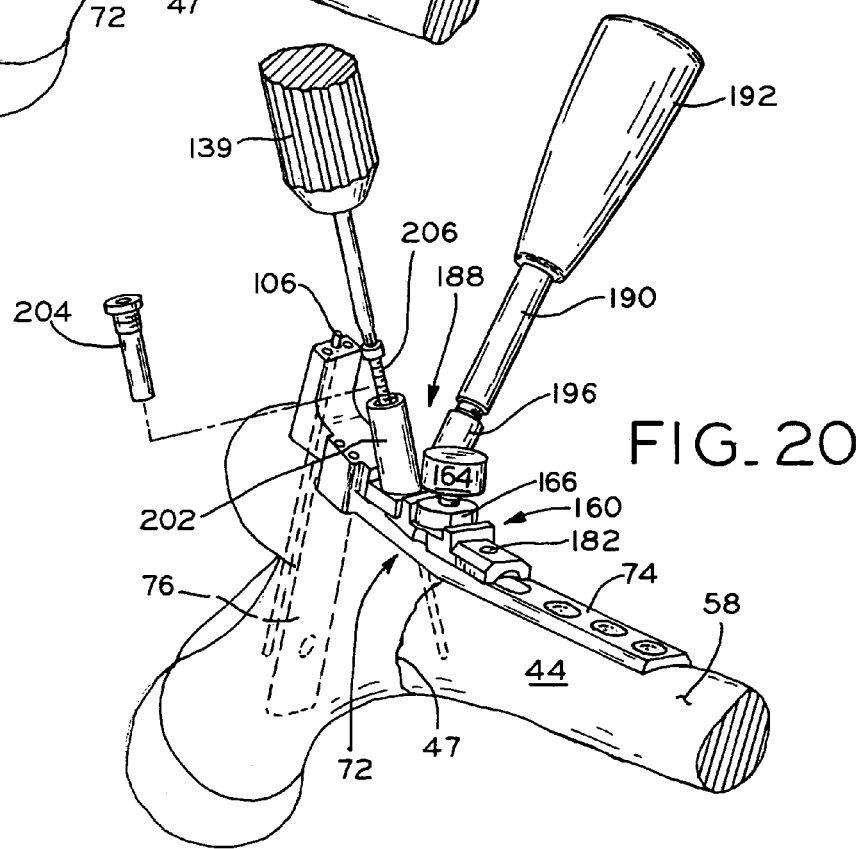
FIG_20

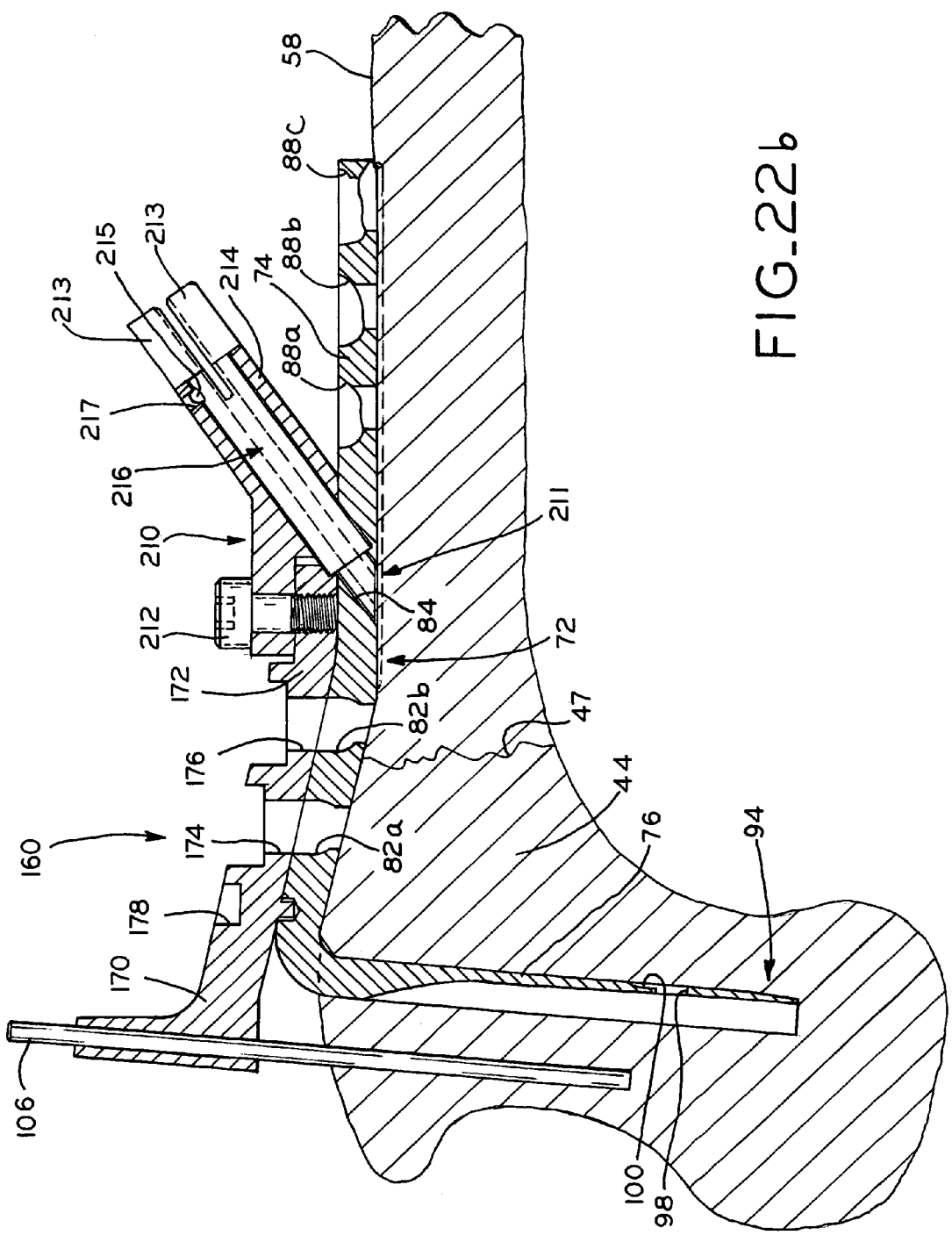

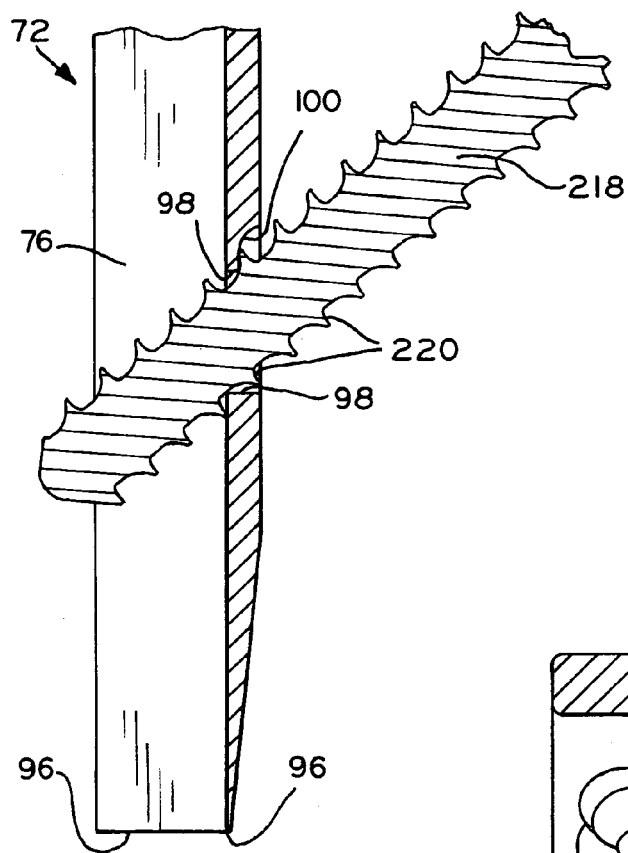
FIG_25
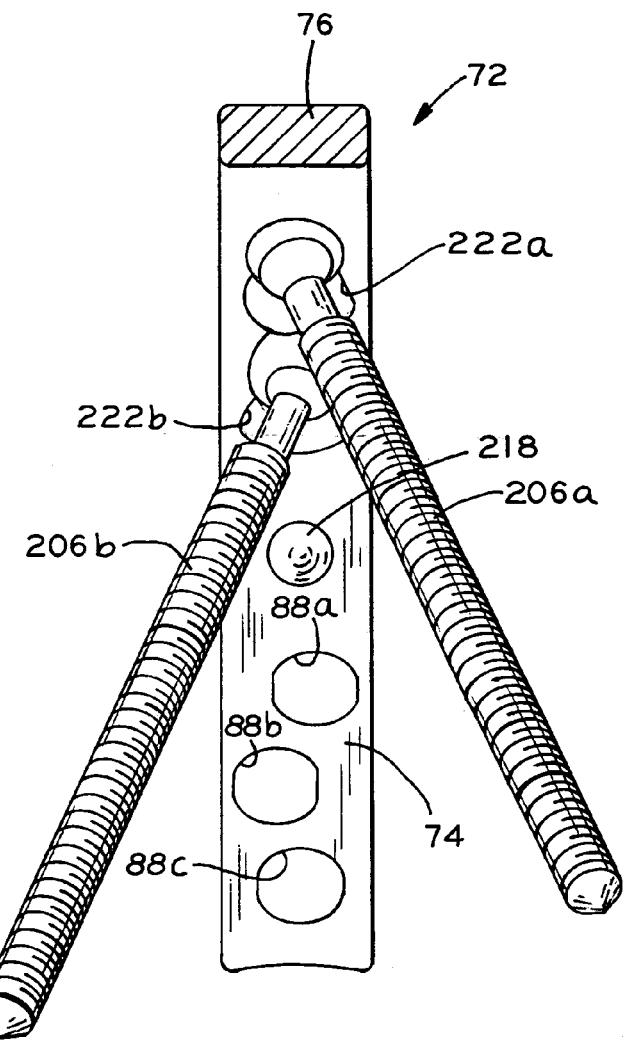
FIG_26

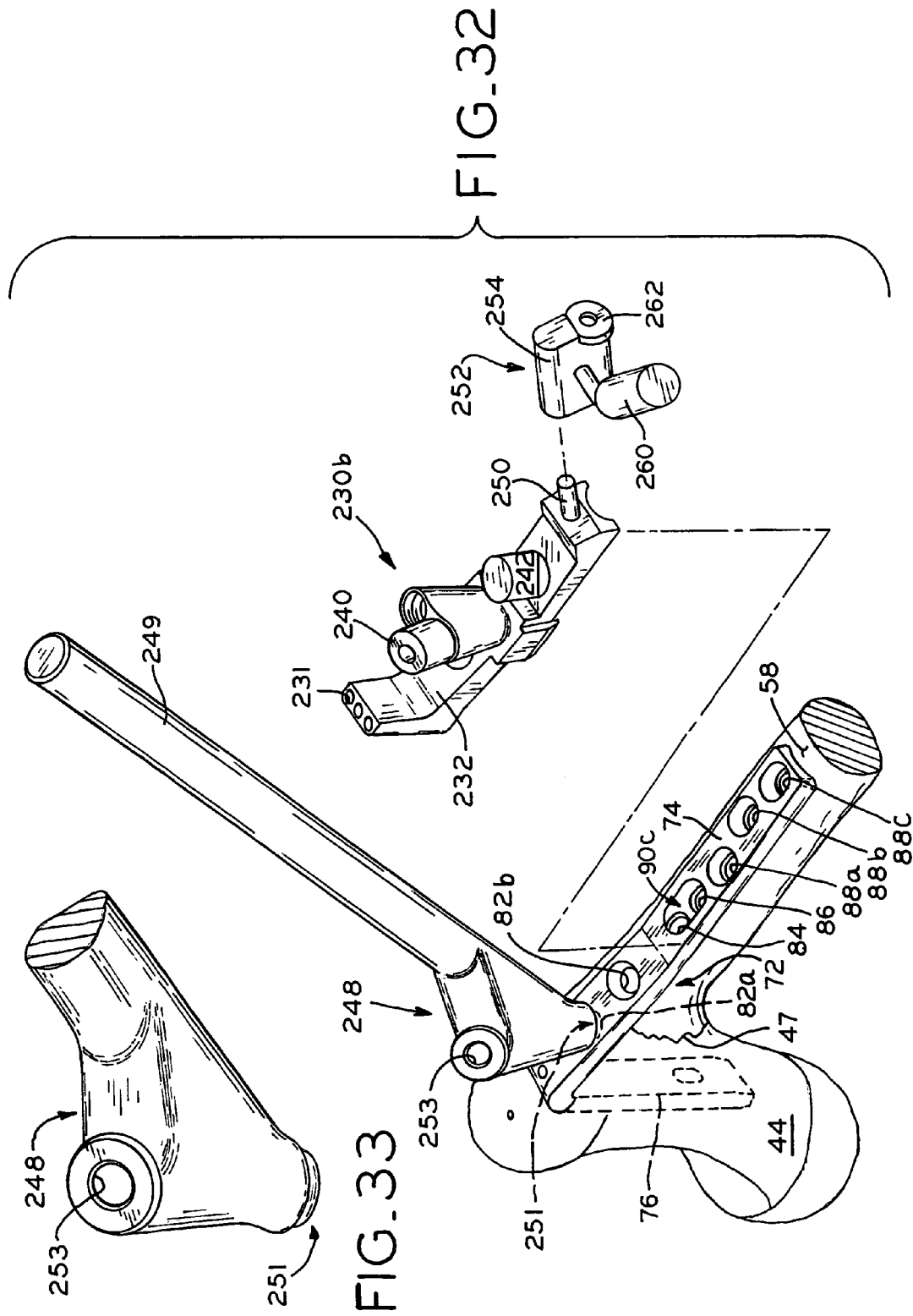

BLADE PLATE AND INSTRUMENTS

BACKGROUND OF THE INVENTION

1. Field of the Invention

The present invention relates to medical implants and associated methods for reducing a bone fracture and supporting the bone while the bone heals, and more particularly, to a blade plate and instruments for securing the blade plate to a bone to reduce a bone fracture.

2. Description of the Related Art

Bone plates are secured to a bone about a fracture in the bone to hold the bone in place while the fracture heals. Additionally, the bone plate may be secured to the bone in a manner in which the bone plate also provides support and/or compression to the bone about the fracture in order to compress the fracture. Typically, such bone plates include a plurality of holes therein for receipt of screws which are inserted into the bone to secure the bone plate to the bone about the fracture to hold the fracture in place. The bone plate may also include a blade extending therefrom for insertion into a channel which has been pre-cut into the bone, in order to support the fragments of the fractured bone and to establish a compressive load about the fracture to compress the fracture.

While known bone plates have proven effective for reducing a bone fracture and compressing the fracture while the bone heals, an improved bone plate, as well as instruments for securing the bone plate to a bone, are desired, for providing improved bone fixation about the fracture, increased patient comfort, and improved accuracy of installation.

SUMMARY OF THE INVENTION

The present invention provides a bone plate, as well as instruments and methods for securing the bone plate to a bone to reduce a bone fracture. The bone plate may be in the form of a blade plate, including a plate portion and a blade portion extending at an angle relative to the plate portion. The plate portion includes a plurality of holes for receipt of bone screws for securing the blade plate to the bone about the bone fracture. A strut screw hole in the plate portion, which is disposed at an angle relative to the plane in which the plate portion is disposed, receives a strut screw therethrough. The strut screw spans the angle between the plate and blade portions, and the end of the strut screw threadingly engages a hole in the blade portion to support the blade portion and to prevent movement of same, and to secure the blade and plate portions of the blade plate about the fracture to compress the fracture.

Additionally, the plate portion includes first and second holes for receiving top screws, the first and second holes including counterbores which are shaped to allow the top screws to be received therethrough at an angle relative to the strut screw to avoid contact between the top screws and the strut screw. Further, the plate portion includes a cross screw hole disposed closely adjacent the strut screw hole through which a cross screw may be inserted, with the head of the cross screw abutting the head of the strut screw to lock the strut screw in position whereby withdrawal of the strut screw outwardly from the bone is prevented.

The plate and blade portions are connected at a bend in the blade plate. The fillet radius of the bend, which is defined interiorly of the bend intermediate the plate and blade portions, is greatly reduced from known designs, allowing closer conformity of the blade plate with the bone surface at the outer edge of the channel in the bone through which the blade is inserted, and minimizing the gap between the blade plate and the bone surface in the area of the bend in the blade plate.

To secure the blade plate to the bone about the fracture, instruments and corresponding methods are also disclosed. One embodiment of such instruments and corresponding methods is briefly described below. A chisel and drill guide assembly is provided, which includes a chisel/drill guide member having at least one slot therein through which a guide wire may be disposed for locating the chisel/drill guide member with respect to the bone surface, and a plate portion extending therefrom which rests against the bone surface. A drill guide, which includes drill guide holes for drilling holes in the bone which correspond to the insertion point of the blade portion of the blade plate, is received within a channel in the chisel/drill guide member. The drill guide is removed after such holes are drilled, and a chisel is inserted through the channel in the chisel/drill guide member and driven into the bone to form a blade insertion channel in the bone about the holes. After the blade insertion channel is formed, the chisel is removed, and a drill or saw blade is inserted into a chamfer slot in the chisel/drill guide member to remove bone material from a corner portion of the bone at the opening of the blade insertion channel, thereby forming a chamfer on the bone to facilitate a closely conforming fit between the fillet radius of the blade plate and the bone at the opening of the blade insertion channel.

After removal of the chisel/drill guide member, an insertion guide is secured to the blade plate and passed over the guide wire. A hammer and impaction handle, or alternatively, a slap hammer, is used to drive the blade portion of the blade plate into the blade insertion channel in the bone. After insertion of the blade portion of the blade plate, screws are inserted through the blade plate and into the bone to reduce and compress the fracture. The number of screws inserted, and the order of insertion thereof, may vary. A top screw drill guide is attached to the insertion guide to facilitate the insertion of a first top screw at an angle relative to the plate portion, after first pre-drilling a guide hole in the bone through the top screw drill guide. The top screw drill guide is then removed from the insertion guide. A strut screw drill guide is then attached to the insertion guide, and, after pre-drilling a hole in the bone, a strut screw is inserted which extends through the bone between the plate portion and the blade portion of the blade plate, the strut screw threadingly engaging the blade portion to secure the blade plate and plate portions about the fracture. An additional top screw, a cross screw, and a plurality of compression screws may also be inserted through the plate portion of the blade plate as needed to further secure the blade plate to the bone for reducing the fracture.

In one form thereof, the present invention provides a bone plate assembly, including a bone plate including first and second extending portions defining an angle therebetween, each of the first and second portions having at least one hole therein; and a screw extending through a hole in one of the first and second portions, the screw threadingly engaging another hole in the other of the first and second portions, wherein the screw spans said angle between the first and second portions.

In another form thereof, the present invention provides a bone plate, including a plate portion and a blade portion extending from one another at an angle and connected to one another at a bend, the bend having a radius defined intermediate the plate portion and the blade portion, the radius dimensioned such that, with the plate portion resting against an outer surface of a bone and the blade portion extending into the bone, the radius fits closely adjacent the outside surface of the bone.

In another form thereof, the present invention provides a method of designing a blade plate from at least one sample bone such that the bone plate conforms to the outer surface of the bone, including the steps of taking a plurality of measurements of the bone surface; generating one of a three-dimensional model and a three-dimensional map of the bone surface; and determining the shape of the bone plate to conform to one of the three-dimensional model and three dimensional map.

In another form thereof, the present invention provides a bone plate, including an elongate plate portion disposed in a plane, the plate portion including first and second holes disposed closely adjacent one another, the first hole disposed through the plate portion at an angle relative to the plane and the second hole disposed through the plate portion substantially perpendicular to the plane; and first and second screws each having a head, the first and second screws respectively disposed through the first and second holes, the head of the second screw positioned to prevent removal of the first screw from the plate portion.

In another form thereof, the present invention provides a bone plate assembly, including a bone plate having elongate plate and blade portions connected to one another at a bend and disposed at an angle with respect to one another, the plate portion having a first hole therein and a second hole therein which is disposed intermediate the first hole and said bend; a strut screw disposed through the first hole and extending toward the blade portion; a top screw disposed through the second hole, the top screw extending angularly to one side of the strut screw.

In another form thereof, the present invention provides a kit, including a chisel having an elongate blade portion; and a chisel and drill guide member, the chisel and drill guide member having a first channel therethrough, the first channel dimensioned to receive the chisel.

In another form thereof, the present invention provides a kit, including a drill guide insert; and a chisel and drill guide member, the chisel and drill guide member having a first channel therethrough, the first channel dimensioned to receive the drill guide insert.

In another form thereof, the present invention provides a method, including the steps of providing a chisel and a chisel guide member, the chisel guide member having a channel therethrough dimensioned to receive the chisel, and a chamfer slot extending therethrough to meet the channel, the chamfer slot disposed at an angle with respect to the channel; locating the chisel guide member against the surface of a bone; inserting the chisel through the channel in the chisel guide member; driving the chisel into the bone to form an insertion channel through at least a portion of the bone, the insertion channel defining an opening at the bone surface having a corner portion; providing a tool; inserting the tool through the chamfer slot of the chisel guide member; and removing bone material from the corner portion with the tool to substantially form a radius in the edge of the bone at the insertion channel opening.

In a further form thereof, the present invention provides a kit, including a bone plate having elongate plate and blade portions disposed at an angle with respect to one another, the plate portion having a plurality of holes therein; an insertion guide member detachably securable to the plate portion of the bone plate; and a screw guide detachably securable to the insertion guide member in alignment with one of the plurality of holes in the plate portion.

In a still further form thereof, the present invention provides a kit, including a bone plate having plate and blade portions disposed at an angle with respect to one another, the plate portion having a long dimension and plurality of holes therein; and an insertion guide member detachably securable to the plate portion of the bone plate, the insertion guide member having at least one screw guide member integral therewith, the screw guide member disposed at an angle with respect to the plate and blade portions.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is a partial sectional view through a bone having a fracture, including a known blade plate assembly secured to the bone;

FIG. 2 is a side view of a known blade plate;

FIG. 3 is a partial sectional view through a bone having a fracture, including a blade plate assembly according to the present invention secured to the bone;

FIG. 4 is a perspective view of a blade plate according to the present invention;

FIG. 5A is a side view of the blade plate of FIG. 4;

FIG. 5B is a side view of an alternative embodiment of the blade plate of FIGS. 4 and 5A;

FIG. 6 is a perspective view of a bone having a fracture, and a guide wire inserted into the bone;

FIG. 7 is a perspective view of a bone to which a chisel/drill guide member is attached, further showing a drill guide insert being inserted within the guide channel of the chisel/drill guide member;

FIG. 8 is a perspective view of the drill guide insert of FIG. 7;

FIG. 12 is a sectional view of a bone to which a chisel/drill guide member is attached, further showing a drill being inserted through the chamfer slot of the chisel/drill guide member to remove bone material from a corner portion of the blade insertion channel in the bone;

FIG. 13 is an exploded view showing a bone having a blade insertion channel formed therein, a blade plate, an insertion guide, and a screw and lock member for securing the insertion guide to the blade plate;

FIG. 14 is a sectional view of the screw and lock member of FIG. 13, taken along line 14-14 of FIG. 13;

FIG. 15 is a perspective view of a bone to which a blade plate and insertion guide is attached, further showing an impaction handle for driving the blade plate into the blade insertion channel in the bone;

FIG. 16 is a perspective view of a bone to which a blade plate and insertion guide is attached, further showing a top screw drill guide attached to the insertion guide and a top screw drill sleeve being inserted into the top screw drill guide;

FIG. 17 is a bottom view of insertion guide of FIG. 16, showing the top screw drill guide attached thereto;

FIG. 18 is a sectional view taken along line 18-18 of FIG. 17;

FIG. 19 is a perspective view of a bone to which a blade plate and insertion guide is attached, further showing a top screw hole being pre-drilled into the bone through the top screw drill guide;

FIG. 20 is a perspective view of a bone to which a blade plate and insertion guide is attached, further showing a top screw being inserted into the bone through the top screw drill guide after removal of the top screw drill sleeve;

FIG. 22b is a sectional view through the bone, blade plate, and insertion guide of FIG. 22a;

FIG. 25 is a sectional view through a portion of the blade portion of a blade plate, showing a strut screw threadedly engaging a blade plate hole in the blade portion of the blade plate;

FIG. 26 is a partial sectional view of a blade plate through which a pair of top screws and a strut screw have been inserted, viewed directly down the strut screw and showing the top screws each disposed at an angle with respect to the strut screw;

FIG. 32 is a perspective view of a bone to which a blade plate is attached, further showing removal of the insertion guide of FIG. 31, and a hand-held top screw drill guide inserted into one of the top screw holes in the blade plate; and FIG. 33 is a partial perspective view of the hand-held top screw drill guide of FIG. 32.7

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 9:
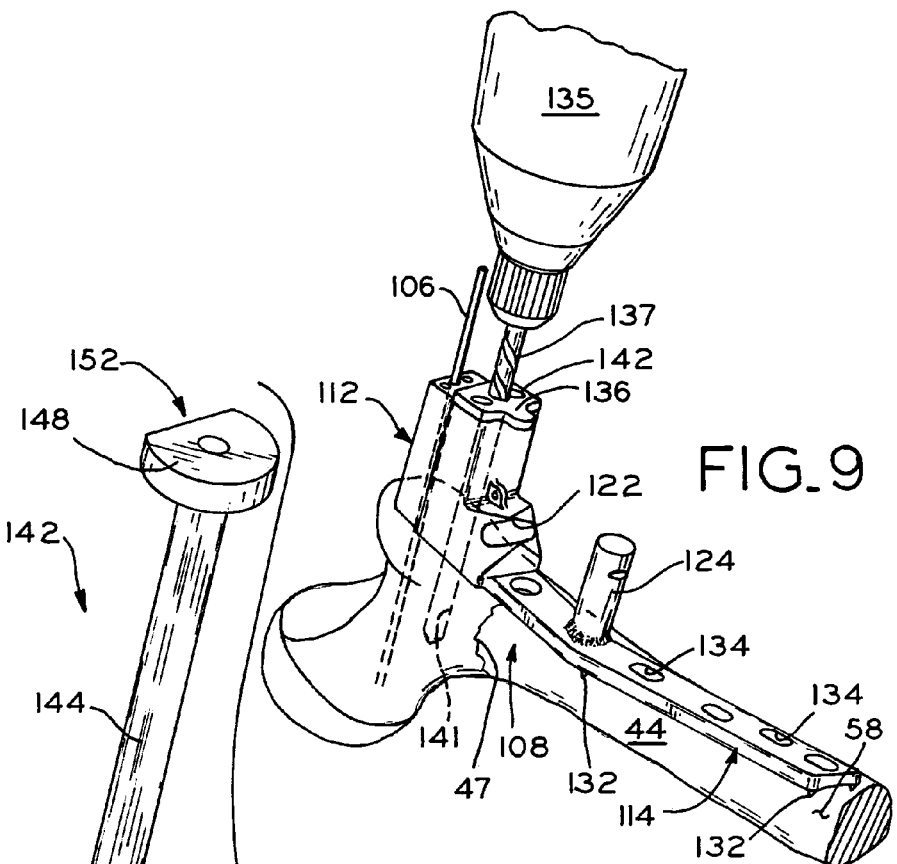
FIG. 9 is a perspective view of a bone to which a chisel/drill guide member is attached, further showing a guide hole being drilled through the drill guide insert.

Referring to FIG. 1, a known bone plate assembly 40 is shown, including bone plate 42 secured to bone 44 by screws 46a-f, which are inserted through holes in bone plate 42 and into bone 44 about fracture 47 to hold the fragments of bone 44 in place until bone 44 heals. Bone plate 42 is shown as a blade plate, including plate portion 48 having a plurality of holes therethrough for receipt of screws 46a-f, and blade portion 50 extending from plate portion 48 to define an angle therebetween. Plate portion 48 and blade portion 50 are connected at bend 52, which defines fillet radius 54 (FIG. 2) intermediate plate portion 48 and blade portion 50. Referring to FIG. 1, it may be seen that, due to the large size of fillet radius 54, a large gap 56 exists between plate portion 48 and outer surface 58 of bone 44 adjacent bend 52, wherein bend 52 projects outwardly of outer surface 58 of bone 44. Screws 46a-f include strut screw 46c, which is disposed through one of the holes in plate portion 48 and extends toward blade portion 50 of blade plate 42 such that end 60 of strut screw 46c abuts blade portion 50.

Referring to FIG. 3, bone plate assembly 70 is shown in accordance with the present invention, including bone plate 72, which is shown as a blade plate secured to bone 44 about fracture 47 to hold the fragments of bone 44 in place and to provide a compressive force about fracture 47. Referring to FIGS. 3 and 4, blade plate 72 includes plate portion 74 and blade portion 76 connected to one another at bend 75. Blade portion 76 extends from plate portion 74 to define an angle therebetween which, as shown in FIGS. 3 and 4, is a slightly obtuse angle. However, blade plate 72 may be shaped such that the angle defined between plate and blade portions 74, 76 may vary from slightly acute to significantly obtuse, or any desired angle, depending on the particular geometry of the bone to which blade plate 72 is to be secured. Additionally, although blade plate 72 is shown in FIG. 3 secured to the proximal femur, it should be understood that blade plate 72 may be appropriately shaped and dimensioned for securing same to the distal femur, or to any other bone having a fracture therein, in order to reduce and compress the fracture, without departing from the present invention.

Referring to FIG. 4, plate portion 74 includes first and second top screw holes 82a, 82b, strut screw hole 84, cross screw hole 86, and a plurality of compression screw holes 88a-c. As shown in FIG. 4, it may be seen that the foregoing holes include respective bores disposed through plate portion 74, as well as generally bowl-shaped counterbores extending partially through the thickness of plate portion 74 which define recesses 90a-f in plate portion 74. Recesses 90a-b of top screw holes 82a, 82b are shown as oval-shaped, with the long dimensions thereof extending generally perpendicular to the long dimension of plate portion 74, and recess 90c of strut screw and cross screw holes 84, 86, as well as recesses 90d-f of compression screw holes 88a-c are also shown as oval-shaped, with the long dimensions thereof extending generally parallel to the long dimension of plate portion 74. Recess 90c encompasses both strut screw hole 84 and cross screw hole 86. Recess 92 is defined in plate portion 74 intermediate first top screw hole 82a and bend 75.

Blade portion 76 includes blade end 94 having a generally U-shaped cross section including three blade edges 96. Alternatively, blade end 94 may have an inverted T-shaped cross section, or any other suitable cross section. Blade portion 76 also includes blade hole 98 having a chamfer therearound which defines ledge 100 around at least a portion of blade hole 98.

Referring to FIGS. 5A and 5B, bend 75 of blade plate 72 includes fillet radius 102 defined intermediate plate portion 74 and blade portion 76, wherein the size of fillet radius 102 is minimized in comparison with known blade plate 42 of FIGS. 1 and 2. Specifically, the size of fillet radius 102 of blade plate 72 is 0.25 inches or less, preferably 0.125 inches, which is reduced from the fillet radius 54 of prior blade plate 42 of FIGS. 1 and 2, which prior fillet radius is typically approximately 0.375 inches. Therefore, referring to FIG. 3, when blade plate 72 is secured to bone 44, the reduced size of fillet radius 102 thereof reduces the gap 56 between plate portion 74 of blade plate 72 and outer surface 58 of bone 44, allowing blade plate 72 to closely conform with outer surface 58 of bone 44.

Referring to FIG. 5A, plate portion 74 may include first segment 78 and second segment 80, which meet at intersection 81, which defines an edge between first and second segments 78, 80. Alternatively, as shown in the embodiment of FIG. 5B, the interface between first and second segments 78, 80 may be curved at 82 whereby intersection 81 is eliminated, such that plate portion 74 of blade plate 72 may conform even more closely with the outer surface 58 of bone 44. Specifically, in the embodiment of FIG. 5B, the interior profile 104 of plate portion 74 is shaped to match the outer surface 58 of a bone to which blade plate 72 is attached, such as the proximal femur shown in FIG. 3. In order to determine the appropriate shape of interior profile 104 of plate portion 74, actual bone specimens may be used. For example, with regard to designing the shape of a blade plate for a proximal femur, a plurality of measurements may taken of the outer surface of proximal femur specimens, followed by generating one or more three-dimensional maps or models of the femurs using a computer, which maps or models are then used to design blade plates having desired shape characteristics, such as the interior profile of plate portion 74 which conforms closely to the outer surface of the proximal femur. The foregoing design method may be used to design blade plates according to the present invention for use with any type of bone to which a blade plate may be secured.

Exemplary methods of securing blade plate 72 to a bone to reduce a fracture in the bone and to compress the fracture, and instruments therefor, will now be described with reference to FIGS. 6-32, in which methods are shown for securing blade plate 72 to a fractured proximal femur. Initially, an incision (not shown) is made in the body, according to a suitable surgical procedure, to create a surgical wound near the fracture in the proximal femur to expose outer surface 58 of bone 44 about fracture 47. As shown in FIG. 6, a Kirschner guide wire 106 is then inserted into bone 44 in a known manner to provide a fixed reference point with respect to bone 44, wherein the free end of guide wire 106 extends outwardly of the wound in the patient.

A chisel/drill guide member 108, shown in FIG. 7, is used to locate and guide the procedure of forming a blade insertion channel 110 (FIG. 13) within bone 44. Chisel/drill guide member 108 includes head portion 112 with plate portion 114 extending therefrom. Head portion 112 includes a plurality of guide wire holes 116 for insertion of guide wire 106 therethrough to properly locate chisel/drill guide member 108 with respect to bone 44. Guide channel 118 also extends through head portion 112 of chisel/drill guide member 108, and includes first key element 120 therein, which is shown in FIG. 7 as a shoulder extending into guide channel 118. Chamfer slot 122 also extends through head portion 112, and is disposed at an angle with respect to guide channel 118, wherein the distal ends of guide channel 118 and chamfer slot 122 meet one another, as shown in FIG. 12. Chisel/drill guide member 108 additionally includes attachment post 124 for attaching handle 126 thereto. Handle 126 includes handle portion 128 for grasping, and quick-connect/disconnect collar 130 for quick attachment and detachment of handle 126 to and from attachment post 124 of chisel/drill guide member 108.

After attaching handle 126 to attachment post 124 of chisel/drill guide member 108, the free end of guide wire 106 is inserted through one of the guide wire channels 116 in head portion 112 of chisel/drill guide member 108. Chisel/drill guide member 108 is then located against outer surface 58 of bone 44 as shown in FIG. 7, wherein barbs 132 extending from plate portion 114 of chisel/drill guide member may bear against outer surface 58 of bone 44 to anchor chisel/drill guide member 108 thereagainst. Plate portion 114 of chisel/drill guide member 108 additionally includes a plurality of reference holes 134 therein to indicate the locations on outer surface 58 of bone 44 at which screws will later extend into bone 44 through blade plate 72.

Referring still to FIG. 7, drill guide insert 136 (see also FIG. 8) is inserted within guide channel 118 of chisel/drill guide member 108. Drill guide insert 136 includes a second key element 138, shown in FIG. 8, as a channel, which mates with first key element 120 of guide channel 118 to ensure that drill guide insert 136 is inserted within guide channel 118 according to a predetermined orientation. Head flange 140 of drill guide insert 136 abuts head portion 112 of chisel/drill guide member 108 at the entrance of guide channel 118. Drill guide insert 136 includes a plurality of bores 142 therein which serve as guides for drilling a plurality of corresponding guide holes within bone 44. Referring to FIG. 9, after chisel/drill guide member 108 is positioned on bone 44 with drill guide insert 136 disposed in guide channel 118 thereof, guide holes are drilled in bone 44 using a tool, such as drill 135 with bit 137, through each of the bores 142 of drill guide insert 136, which correspond to the location of blade insertion channel 110 within bone 44. After such holes are drilled, drill guide insert 136 is removed from guide channel 118 of chisel/drill guide member 108.

Figures 10, 11:
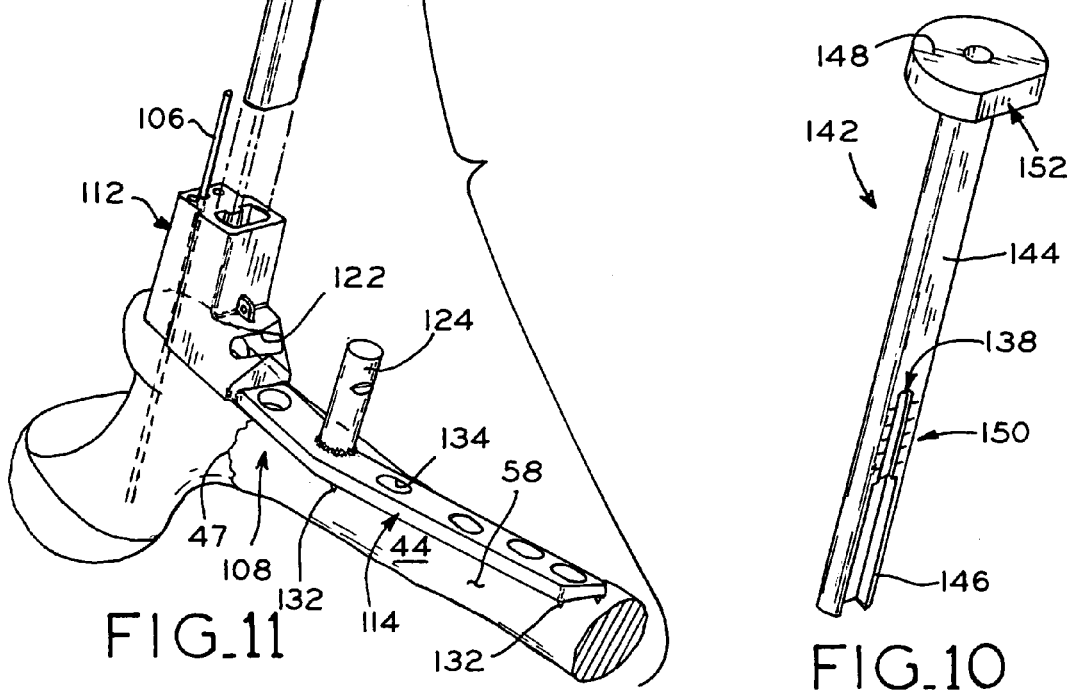
FIG. 10 is a perspective view of a chisel.
FIG. 11 is a perspective view of a bone to which a chisel/drill guide member is attached, further showing the chisel of FIG. 10 being driven into the guide channel of the chisel/drill guide member to form a blade insertion channel in the bone.

Chisel 142, shown in FIGS. 10 and 11, includes stem portion 144 having blade 146 at one end, and head 148 at the other end thereof opposite blade 146. Stem portion 144 of chisel 142 includes a second key element 138, shown as a channel, which is adapted to mate with first key element 120 within guide channel 118 of chisel/drill guide member 108 when blade 146 and stem portion 144 of chisel 142 are inserted therethrough. The engagement between first key element 120 of guide channel 118 and second key elements 138 of either drill guide insert 136 or chisel 142, respectively, insures that drill guide insert 136 and chisel 142 are each inserted into guide channel 118 according only to a desired orientation, thereby preventing drill guide insert 136 and chisel 142 from being inserted upside down, for example, within guide channel 118. Alternatively, guide channel 118 and each of drill guide insert 136 and chisel 142 may be otherwise cooperatively shaped or dimensioned such that drill guide insert 136 and chisel 142 may be inserted into guide channel 118 only according to a single, desired orientation. For example, guide channel 118 may define a hemispherical opening, and drill guide insert 136 and chisel 142 may have cooperating hemispherical profiles.

After chisel 142 is inserted through guide channel 118 in chisel/drill guide member 108 as shown in FIG. 11, head 148 of chisel 142 is impacted with a hammer, mallet, or slap hammer to drive blade 146 of chisel 142 into bone 44 to form blade insertion channel 110 within bone 44. Chisel 142 may additionally include depth markings 150 thereon, shown in FIG. 10, which correspond to the depth into bone 44 to which blade 144 should be driven in order to result in a desired depth of blade insertion channel 110. Additionally, as shown in FIG. 11, head 148 of chisel 142 includes a flattened, cut-away portion at 152, which is faces guide wire 106 in order to prevent potentially interfering contact between head 148 of chisel 142 and guide wire 106 as chisel in driven into bone 44. After chisel 142 is driven into bone 44 to form blade insertion channel to a desired depth, chisel 142 is removed from guide channel 118 of chisel/drill guide member 108 to allow access to blade insertion channel 110 in bone 44.

Referring to FIG. 12, blade insertion channel 110 includes opening 154 at outer surface 58 of bone 44, which opening 154 includes corner portion 156. A suitable tool, such as drill 135 with bit 137, for example, is inserted through chamfer slot 122 in head portion 112 of chisel/drill guide member 108, and is driven against corner portion 156 of opening 154 of blade insertion channel 110 to remove bone material from corner portion 156 and thereby provide opening 154 of blade insertion channel 110 with a flattened, chamfered edge 158. Chamfered edge 158 allows fillet radius 102 at bend 75 in blade plate 72 (shown in FIGS. 5A and 5B) to fit closely adjacent chamfered edge 158 of bone 44 adjacent opening 154 of blade insertion channel 110 in bone 44. After bone material from corner portion 156 is removed as discussed above, the tool is removed, and then chisel/drill guide member 108 is removed from bone 44 and detached from the free end of guide wire 106.

After blade insertion channel 110 is formed in bone 44 as shown in FIG. 13, blade plate 72 is secured to bone 44 as shown in FIGS. 13-32. Referring first to FIG. 13, insertion guide 160, according to one embodiment of the present invention, is secured to blade plate 72 by screw and lock member 162 (FIG. 14), which includes thumb screw 164 and lock member 166. As shown in FIG. 13, locking fingers 168 of lock member 166 are inserted through second drill guide hole 176 of insertion guide 160, and extend into top screw hole 82b in blade plate 172. Upon threading thumb screw 164 through lock member 166, locking fingers 168 are spread apart to frictionally engage top screw hole 82b to secure insertion guide 160 to blade plate 72.

Insertion guide 160 generally includes head portion 170 having a plurality of holes 180 therein through which guide wire 106 may be inserted, and also includes impaction recess 178. Plate portion 172, extending from head portion 170, includes first and second drill guide holes 174, 176, as well as strut screw drill guide attachment hole 182. Optionally, head portion 172 of insertion guide 160 may include a stud (not shown) which may fit within recess 92 (FIG. 4) of blade plate 72 to aid in locating insertion guide 160 onto blade plate 72.

Referring to FIGS. 13 and 15, after insertion guide 160 is attached to blade plate 72, guide wire 106 is inserted through one of holes 180 in head portion 170 of insertion guide 160, and blade end 94 of blade plate 72 is aligned with blade insertion channel 110 in bone 144. Thereafter, impaction handle 184 is inserted into impaction recess 178, and head 186 of impaction handle 184 is struck by a hammer or mallet to drive blade portion 76 of blade plate 72 into blade insertion channel 110 of bone 44. Alternatively, a slap hammer (not shown) may be used to drive blade portion 76 of blade plate 72 into blade insertion channel 110 of bone 44.

Referring to FIGS. 16-18, top screw drill guide 188 is attached to insertion guide 160 with handle 190. Handle 190 includes handle portion 192 and threaded end 194. As shown in FIGS. 16-17, threaded end 194 of handle 190 is inserted through handle guide cylinder 196 of top screw drill guide 188. Threaded end 194 of handle 190 engages one of the indentations 198 formed in plate portion 172 of insertion guide 160 on either side of first and second drill holes 174, 176, and additionally, flange 200 of top screw drill guide abuts an opposite side of plate portion 172 of insertion guide 160 to secure top screw drill guide 188 to insertion guide 160.

Top screw drill guide 188 additionally includes top screw guide cylinder 202 which, as shown in FIG. 16, is disposed at an angle with respect to the long dimension of blade portion 76, and is also disposed substantially perpendicular to the long dimension of plate portion 74 of blade plate 72, when top screw drill guide 188 is attached to insertion guide 160. Top screw drill sleeve 204 is threadingly inserted into top screw guide cylinder 202 as shown in FIGS. 16 and 18, and, as shown in FIG. 19, drill 135 with bit 137 is used to drill a guide hole through top screw drill sleeve 204 into bone 44, which hole is disposed at an angle with respect to the long dimension of blade portion 76, and is disposed substantially perpendicular to the long dimension of plate portion 74 of blade plate 72.

After such guide hole is drilled, top screw drill sleeve 204 is removed from top screw guide cylinder 202 as shown in FIG. 20, and a suitable tool, such as screwdriver 139, is used to insert top screw 206a through top screw guide cylinder 202, top screw hole 82a of blade plate 72 (FIG. 4), and into the pre-drilled guide hole in bone 44. The foregoing procedure is used when top screw 206a is a self tapping screw. Alternatively, if a non-self tapping top screw is used, a tap sleeve (not shown) may be inserted into top screw guide cylinder 202, and a bone tap (not shown) may be used to pre-tap the guide hole in the bone for later insertion of a non-self tapping top screw.

Figure 21:
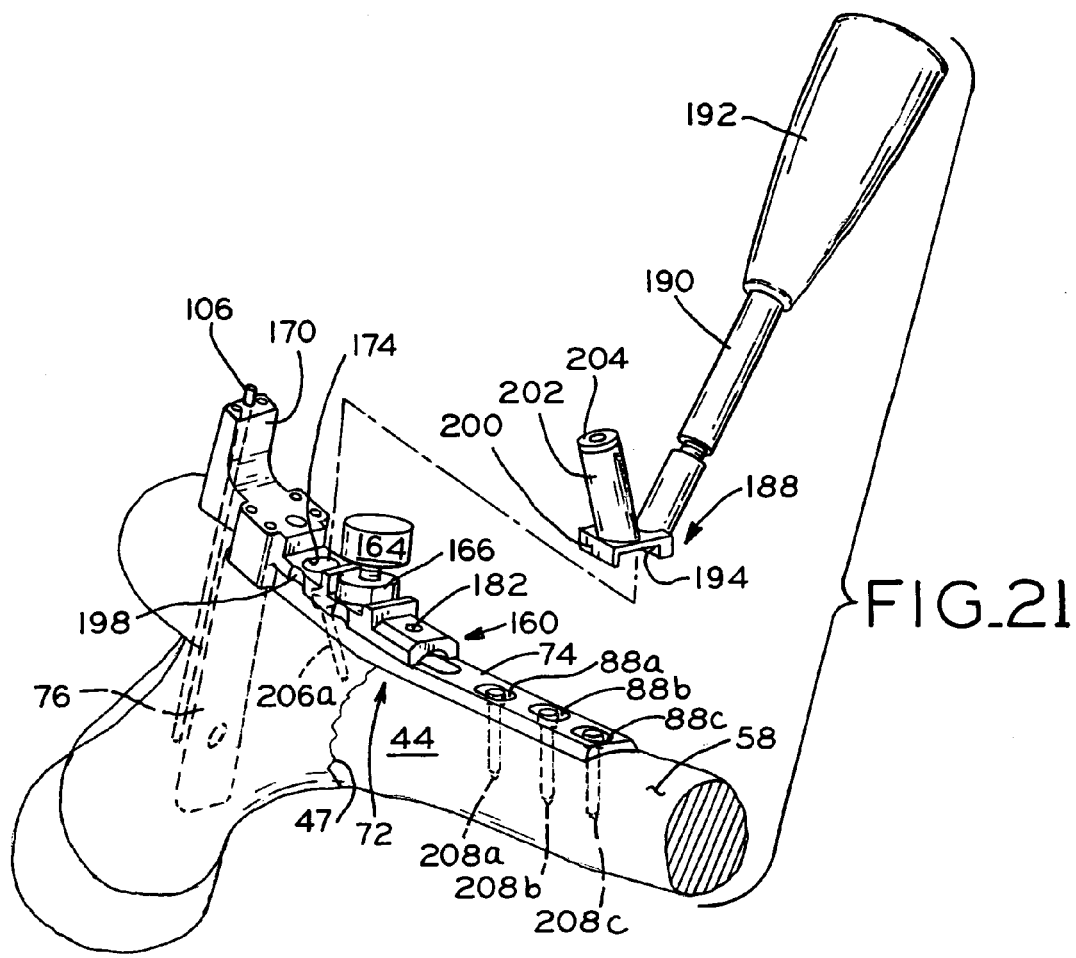
FIG. 21 is a perspective view of a bone to which a blade plate and insertion guide is attached, further showing removal of the top screw drill guide, and a plurality of compression screws inserted through the blade plate into the bone.

Referring to FIG. 21, after top screw 206a is inserted through top screw hole 82a of blade plate 72 and into bone 44, top screw drill guide 188 may be detached from insertion guide 160 by rotating handle 190 to disengage threaded end 194 of handle 190 from indentation 198 of insertion guide 160.

Still referring to FIG. 21, after blade plate 72 has been initially secured to bone 44 by top screw 206a, compression screws 208a-c may be inserted into bone 44 in a suitable manner through compression screw holes 88a-c of blade plate 72 to further secure blade plate 72 to bone 44 and to compress bone 44 about fracture 47 to reduce fracture 47. However, it should be noted that compression screws 208a-c may be inserted into bone 44 through compression screw holes 88a-c in blade plate 72 at any other suitable or desired time during the procedure described herein.

Figure 22A:
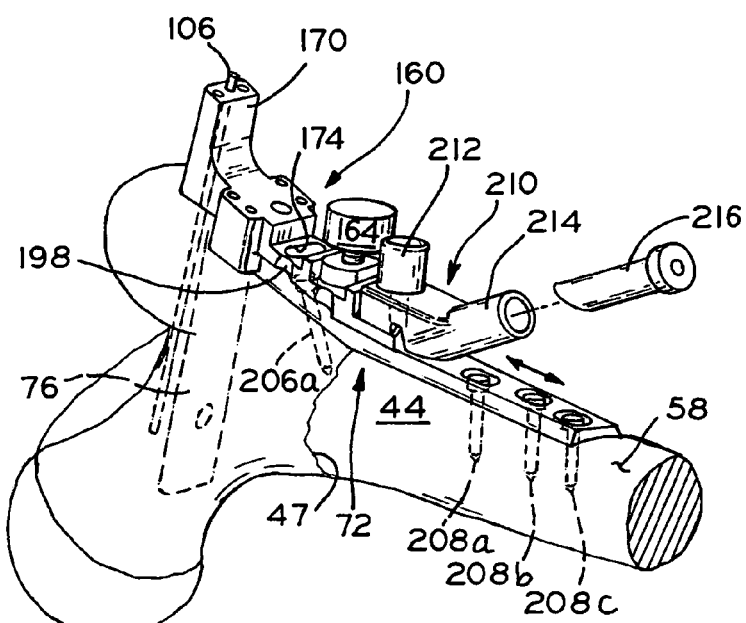
FIG. 22a is a perspective view of a bone to which a blade plate and insertion guide is attached, further showing a strut screw drill guide attached to the insertion guide, and a strut screw drill sleeve being inserted into the strut screw drill guide.
Figure 23:
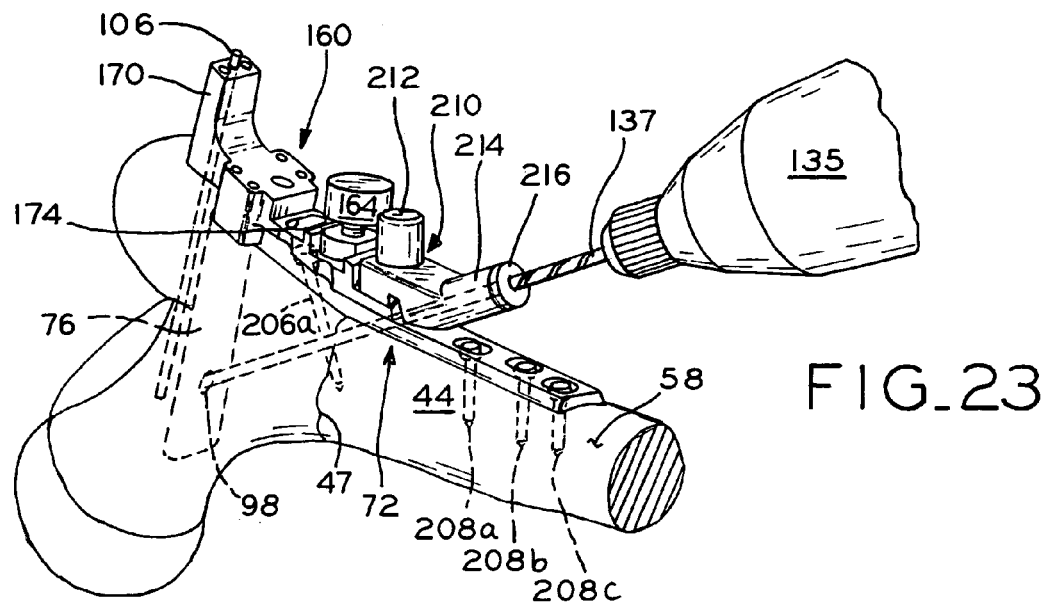
FIG. 23 is a perspective view of a bone to which a blade plate and insertion guide is attached, further showing a strut screw hole being pre-drilled into the bone through the strut screw drill guide.

Referring now to FIG. 22a, strut screw drill guide 210 is attached to strut screw drill screw guide attachment hole 182 (FIG. 13) of insertion guide 160 by thumb screw 212, and includes strut screw guide cylinder 214 which is disposed at an acute angle with respect to blade plate 72 when strut screw drill guide 210 is attached to insertion guide 160. Strut screw drill guide 210 may slide slightly along insertion guide 160 in directions parallel to the long dimension of plate portion 74 of blade plate 72, as indicated by the arrows in FIG. 22, to orient strut screw drill guide 210 with strut screw hole 84 of blade plate 72. Strut screw drill sleeve 216 is inserted into strut screw guide cylinder 214 as shown in FIG. 22*a*, and, as shown in FIG. 23, drill 135 with bit 137 is used to drill a guide hole through strut screw drill sleeve 216, strut screw hole 84 in blade plate 72 (FIG. 4), and bone 44 toward blade hole 98 in blade portion 76 of blade plate 72.

Referring to FIG. 22*b*, it may be seen that strut screw drill sleeve 216 includes a reduced diameter, angled end 211 which extends through strut screw hole 84 of blade plate 72. Angled end 211 is angled to rest against outer surface 58 of bone 44 to guide bit 137 of drill 135 (FIG. 23), such that skiving of bit 137 of drill 135 against outer surface 58 of bone 44 is prevented when the strut screw guide hole is drilled into bone 44, as described above. Additionally, strut screw drill sleeve 216 may include a pair of flexible cylinder sub-portions 213, one of same including stud 215 which releaseably engages recess 217 in strut screw guide cylinder 214 when strut screw drill sleeve 216 is inserted therein, in order to detachably lock strut screw drill sleeve 216 within strut screw guide cylinder 214.

Figure 24:
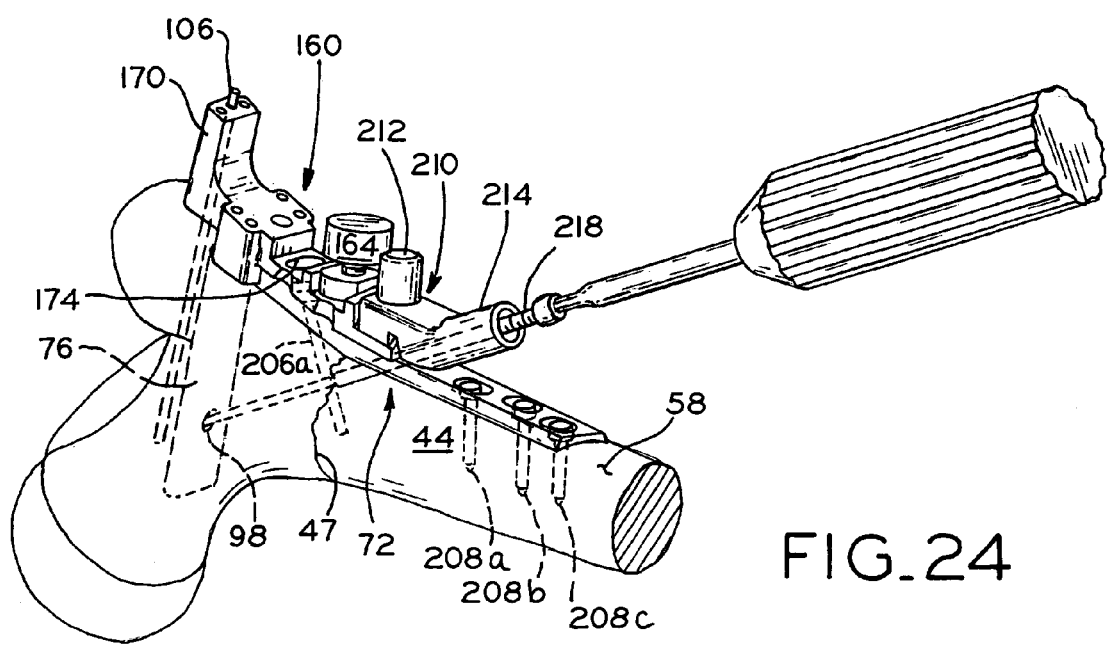
FIG. 24 is a perspective view of a bone to which a blade plate and insertion guide is attached, further showing a strut screw being inserted into the bone through the strut screw drill guide.

Referring to FIG. 24, after removal of strut screw drill sleeve 216, strut screw 218 is inserted through strut screw guide cylinder 214 of strut screw drill guide 210, and through strut screw hole 84 (FIG. 4) of blade plate 72 into bone 44. The foregoing procedure is used when strut screw 218 is a self tapping screw. Alternatively, if a non-self tapping strut screw is used, a tap sleeve (not shown) may be inserted into strut screw guide cylinder 214, and a bone tap (not shown) may be used to pre-tap the hole in the bone for later insertion of a non-self tapping strut screw.

Additionally, as shown in FIG. 25, threads 220 of strut screw 218 engage ledge 100 of blade hole 98 in blade portion 76 of blade plate 72 to thereby threadingly engage strut screw 218 with blade portion 76 of blade plate 72. Blade portion 76 of blade plate 72 may thus be drawn slightly toward plate portion 74 of blade plate 72 by tightening strut screw 218 in order to compress bone 44 about fracture 47 and support the fragments of bone 44. Additionally, strut screw 218 supports blade portion 76 and prevents movement of blade portion angularly with respect to plate portion 74, and also torsionally about the long axis of blade portion 76. After strut screw 218 is thus inserted through strut screw hole 84 of blade plate 72 through bone 44 and into blade hole 98 in blade portion 76 of blade plate 72, strut screw drill guide 210 is detached from insertion guide 160 by loosening thumb screw 212. Optionally, after the strut screw guide hole is drilled into bone 44, strut screw drill guide 210 may be detached from insertion guide 160, as described above, before strut screw 218 is inserted through strut screw hole 84 of blade plate 72 through bone 44.

A second top screw 206*b* (FIG. 26) may be inserted through top screw hole 82*b* of blade plate 72 into bone 44 after detaching screw and lock member 162 from second drill hole 176 (FIG. 13) of insertion guide 160. Thereafter, top screw drill guide 188 may be attached to insertion guide 160 as described above adjacent second drill guide hole 176, and a second top screw 206*b* may be inserted through top screw drill hole 82*b* into bone 44 according to the procedure described above with regard to top screw 206*a*. Optionally, after removal of insertion guide 160, a separate hand-held top screw drill guide 248, such as that shown in FIG. 30, may be used for insertion of a second top screw 206*b* through top screw hole 82*b* of blade plate 72 into bone 44.

As shown in FIG. 26, top screw holes 82*a*, 82*b* of blade plate 72 include second counterbores 222*a*, 222*b* extending partially through the thickness of plate portion 74 opposite first counterbores 90*a*, 90*b* (FIG. 4), which allow top screws 206*a*, 206*b* to be inserted through top screw holes 82*a*, 82*b* at an angle with respect to the long dimension of blade portion 76, and substantially perpendicular to the long dimension of plate portion 74, of blade plate 72. In this manner, as shown in FIG. 26, strut screw 218 may extend between top screws 206*a*, 206*b*, with top screws 206*a*, 206*b* disposed at an angle with respect to strut screw 218.

Figure 27:
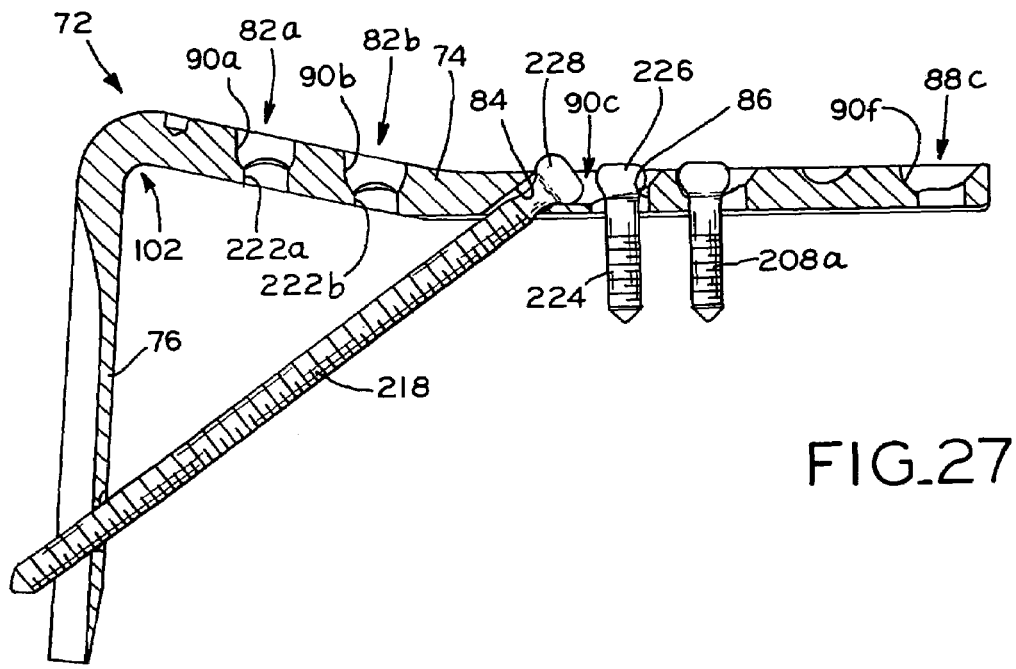
FIG. 27 is a sectional view through a blade plate, showing a cross screw inserted through the cross screw hole in the blade plate, the cross screw being spaced from the head of the strut screw.
Figure 28:
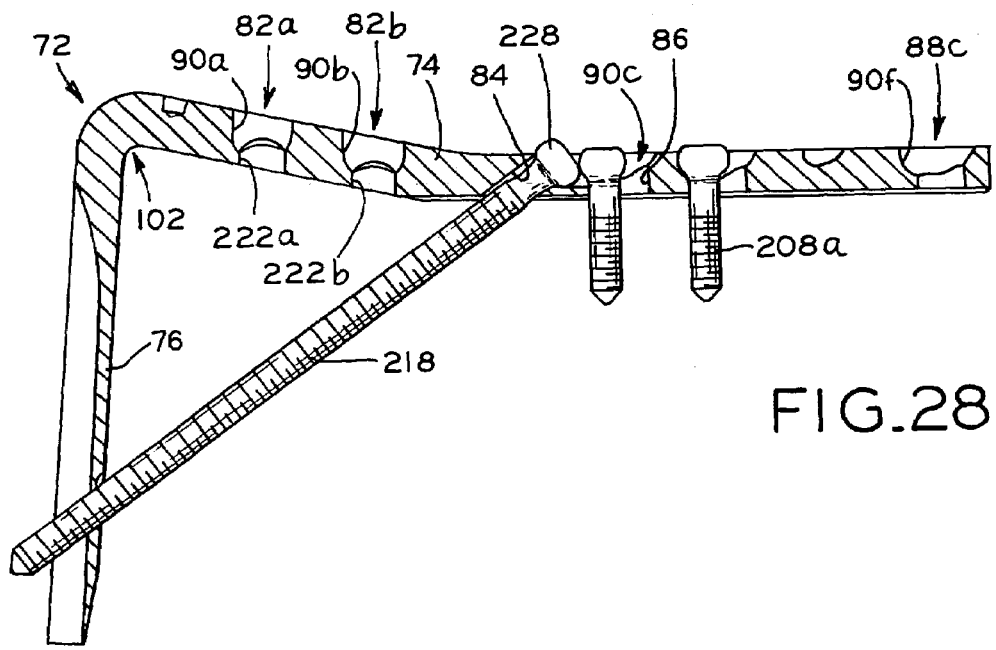
FIG. 28 is a sectional view through a blade plate, showing a cross screw inserted through the cross screw hole in the blade plate, the head of the cross screw abutting the head of the strut screw to lock the strut screw in position.

Referring to FIG. 27, cross or lock screw 224 may be inserted through cross screw hole 86 into bone 44 in a suitable manner, such that head 226 of cross screw 224 is spaced from head 228 of strut screw 218 wherein head 226 of cross screw 224 still prevents removal of strut screw 218 from bone 44. Alternatively, as shown in FIG. 28, and due to the increased size of cross screw hole 86, cross screw 224 may be inserted through cross screw hole 86 into bone 44 such that head 226 of cross screw 224 abuts head 228 of strut screw 218, wherein heads 226, 228 of cross screw 224 and strut screw 218, respectively, are each at least partially disposed within recess 90*c*. In this manner, the abutment between heads 226, 228 of cross screw 224 and strut screw 218, respectively, locks strut screw 218 in position and prevents any withdrawal of strut screw 218 outwardly of plate portion 74 of blade plate 72.

With respect to the above-described procedure for securing blade plate 72 to bone 44 about fracture 47, it should be understood that the order of the particular steps thereof may be modified as desired, depending upon the particular bone to which blade plate 72 is attached, the location and orientation of fracture 47 in bone 44, and other factors.

Figure 29:
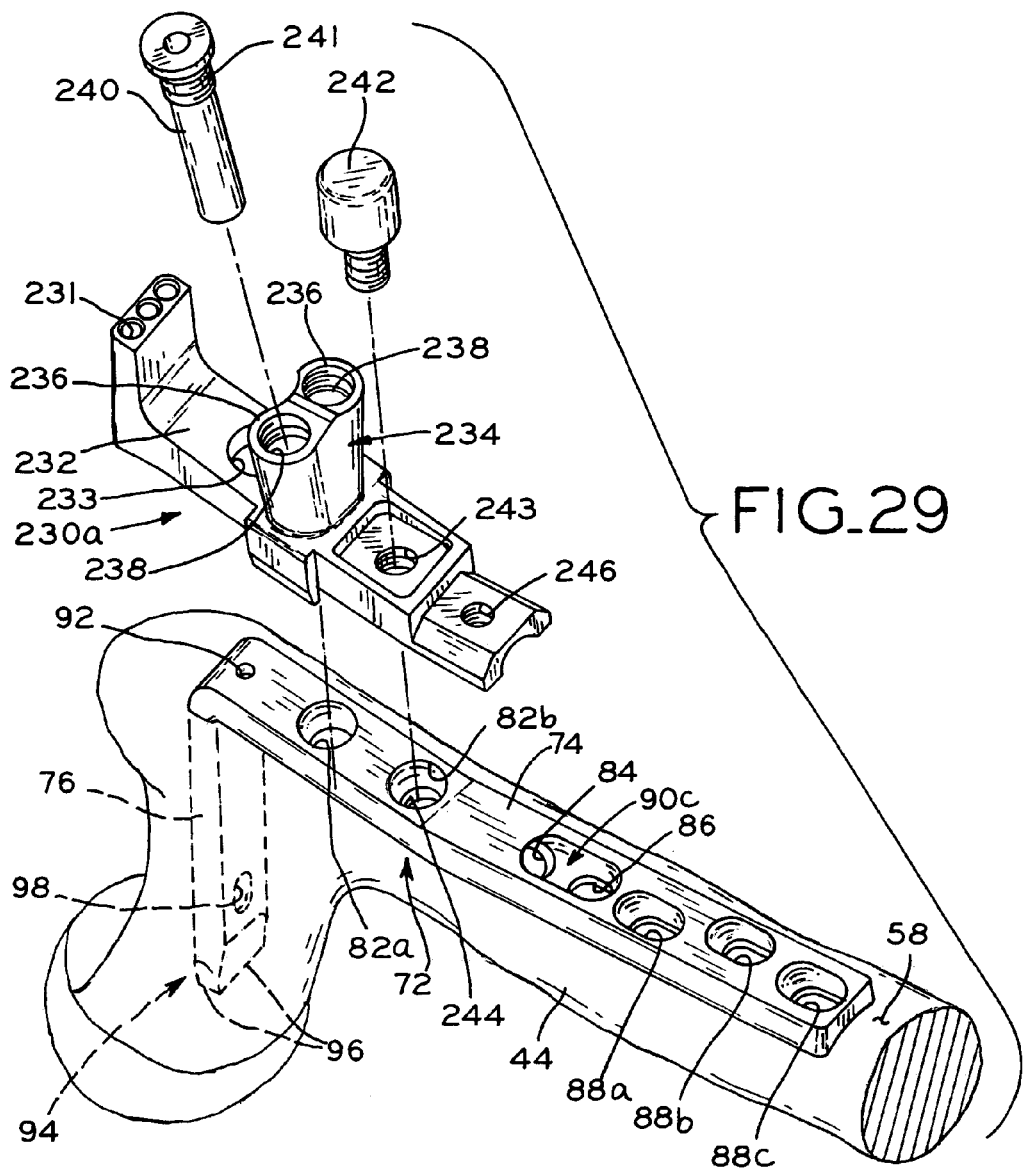
FIG. 29 is a perspective view of a bone to which a blade plate is attached, further showing an insertion guide, top screw drill sleeve, and a thumb screw for securing the insertion guide to the blade plate, according to another embodiment of the present invention.

Referring to FIG. 29, a second embodiment of an insertion guide is shown. Insertion guide 230*a* includes plate portion 232 with holes 231 for receipt of guide wire 106 (not shown) therethrough, and impaction recess 233. Plate portion 232 additionally includes integral top screw drill guide 234, including a pair of top screw guide cylinders 236 which are each disposed at an angle with respect to the long dimensions of blade portion 76 of blade plate 72, as well as plate portion 232 of insertion guide 230*a*. Top screw guide cylinders 236 additionally include threads 238 for positively securing top screw drill sleeves 240 therewithin, wherein threads 241 of top screw drill sleeves 240 engage threads 238 of top screw guide cylinder 236. Insertion guide 230*a* additionally includes attachment hole 243 for receipt of thumb screw 242 for attaching insertion guide 230*a* to blade plate 72, wherein top screw hole 82*b* of blade plate 72 may include threads 244 for engagement with the threads of thumb screw 242. Additionally, strut screw drill guide 210 (FIGS. 22*a*-24) may be attached to strut screw drill guide hole 246 provided in plate portion 232 of insertion guide 230*a*, for drilling a strut screw guide hole in bone 44 and for inserting strut screw 218 through blade plate 72 and into bone 44, also as described above. Insertion guide 230*a* is otherwise used in a similar manner as insertion guide 160, described above, to secure blade plate 72 to bone 44.

Figure 30:
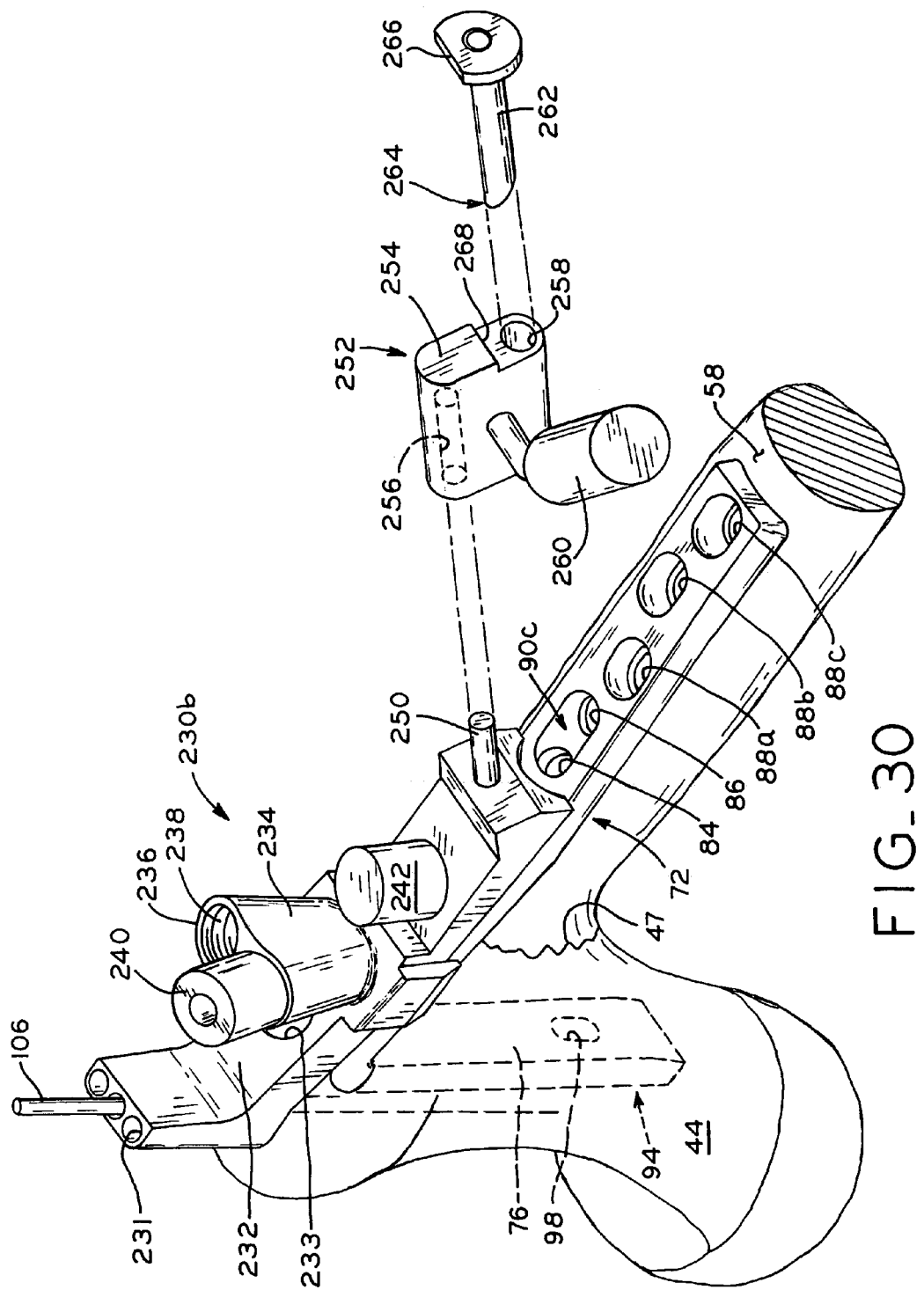
FIG. 30 is a perspective view of a bone to which a blade plate is attached, further showing an insertion guide according to a further embodiment of the present invention, and also showing a strut screw drill guide and strut screw drill sleeve.
Figure 31:
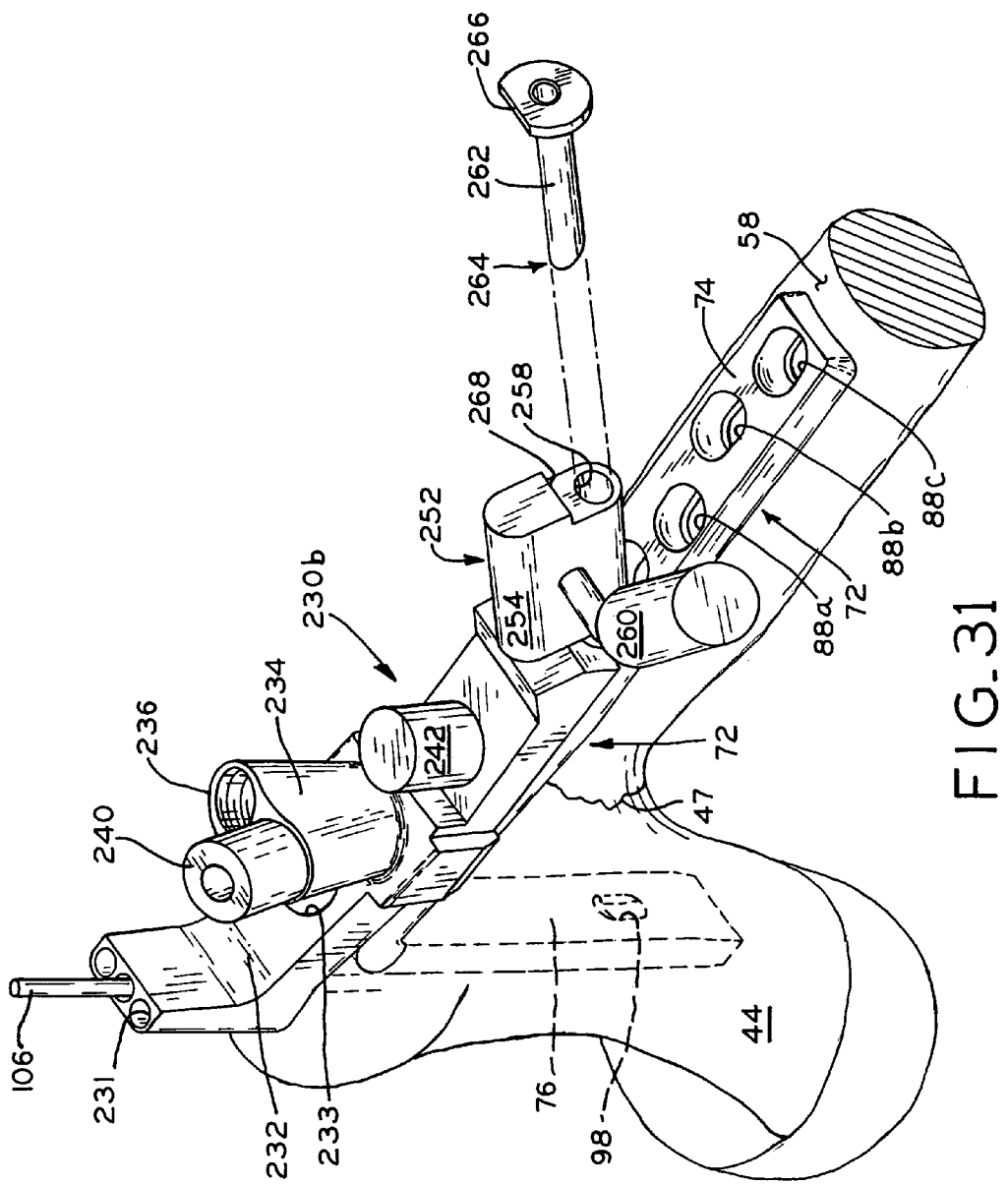
FIG. 31 is a perspective view of a bone to which a blade plate is attached, further showing the insertion guide of FIG. 30, and a strut screw drill sleeve being inserted into the strut screw drill guide.

Referring to FIGS. 30 and 31, a third embodiment of an insertion guide is shown. Insertion guide 230*b* is similar to insertion guide 230*a*, described above, and is used in a similar manner, except as described below. Insertion guide 230*b* lacks strut screw drill guide hole 246 of insertion guide 230*a*, but rather includes strut screw drill guide post 250 extending angularly from plate portion 232 of insertion guide 230*b*. Strut screw drill guide 252 fits onto strut screw drill guide post 250 for guiding the insertion of strut screw 218 through blade plate 72 into bone 44. Strut screw drill guide 252 includes housing 254 with bore 256 therein, into which strut screw drill guide post 250 of insertion guide 230b extends, and also includes strut screw guide bore 258. Handle 260 extends from housing 254 for grasping and manipulating strut screw drill guide 252.

Referring additionally to FIG. 31, strut screw drill sleeve 262 may be inserted into strut screw guide bore 258, and is used as a guide for pre-drilling a strut screw guide hole into bone 44, as described above in connection with the foregoing embodiments. Strut screw drill sleeve 262 includes angled end 264 which contacts outer surface 58 of bone 44 to prevent skiving of the drill bit relative to outer surface 58 of bone 44. Additionally, strut screw drill sleeve 262 includes flat 266 which abuts face 268 of housing 254 of strut screw drill guide 252, such that strut screw drill sleeve 262 may only be inserted through strut screw guide bore 258 in an orientation in which angled end 264 rests against outer surface 58 of bone 44. As also described above in connection with the foregoing embodiments, strut screw drill sleeve 262 is removed after the strut screw guide hole is drilled in bone 44 to allow insertion of a self-tapping strut screw 218 into bone 44 through blade plate 72. Alternatively, a tap (not shown) may be inserted through strut screw guide bore 258 into the strut screw guide hole in bone 44, followed by insertion of a non-self tapping strut screw into bone 44 through blade plate 72.

As shown in FIGS. 32 and 33, after removal of insertion guide 230b from blade plate 72 following insertion of one of top screws 206a, 206b (not shown), according to the procedure described above in connection with the foregoing embodiment, a separate hand-held top screw drill guide 248 may be used to drill a guide hole into bone 44 for a second top screw 206a, 206b, and for guiding insertion of the second top screw 206a, 206b through blade plate 72 and into bone 44. Hand-held top screw drill guide 248 includes handle 249, drill guide bore 253, and shaped head 251 dimensioned for close fitting within top screw holes 82a, b of blade plate 72.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone plate assembly, comprising:
  a bone plate including first and second extending portions defining an angle therebetween, said first portion forming an elongate plate portion having a plate portion longitudinal axis extending along the longest dimension of said elongate plate portion and a plurality of holes therein, said second portion forming an elongate blade portion having a blade portion longitudinal axis extending along the longest dimension of said elongate blade portion, at least one hole therein, and a blade end, said blade portion longitudinal axis transverse to said plate portion longitudinal axis, said blade end having a tapered blade edge tapering along at least a portion of said longitudinal axis of said elongate blade portion, said blade portion have a first cross-section taken at a point on said blade portion longitudinal axis furthest from said plate portion and a second cross-section taken at a point on said blade portion longitudinal axis nearer said plate portion than said first cross-section, said first cross-section being less than said second cross-section, wherein said blade end facilitates the insertion of said elongate blade portion into a bone; and
  a screw extending through a said hole in one of said first and second portions, said screw threadingly engaging another said hole in the other of said first and second portions, and an intermediate portion of said screw between said at least one hole in said first extending portion and said at least one hole in said second extending portion capable of engaging bone, wherein said screw spans said angle between said first and second portions.

2. The bone plate assembly of claim 1, wherein said screw extends through one of said plurality of holes in said plate portion, and engages said at least one hole in said blade portion, wherein said screw extends through said plate portion to engage said at least one hole in said blade portion.

3. The bone plate assembly of claim 2, wherein said at least one hole in said blade portion includes a ledge about at least a portion of the periphery thereof, said screw threadingly engaging said ledge.

4. The bone plate assembly of claim 1, wherein said first and second portions are placed in slight compression by said threaded engagement between said screw and said hole in said second portion.

5. The bone plate of claim 1, wherein said angle has a radius dimensioned such that, with said first extending portion resting against an outer surface of a bone and said second extending portion extending into the bone, said radius fits closely adjacent the outside surface of the bone.

6. The bone plate of claim 5, wherein said radius is about 0.25 inches or less.

7. The bone plate assembly of claim 1, wherein said first cross-section comprises a substantially U-shaped cross-section.

8. A bone plate assembly, comprising:
  a bone plate having elongate plate and blade portions connected to one another at a bend and disposed at an angle with respect to one another, said plate portion having a first hole therein and a second hole therein which is disposed intermediate said first hole and said bend, said second hole including first and second counterbores extending into opposite sides of said plate portion about said second hole, said elongate plate portion having a longitudinal axis;
  a strut screw disposed through said first hole and extending toward said blade portion, said strut screw having a longitudinal axis, said longitudinal axis of said elongate plate portion and said longitudinal axis of said strut screw forming a plane; and
  a top screw disposed through said second hole, said top screw extending angularly away from said plane, wherein said first and second counterbores of said second hole of said plate portion allows said top screw to be disposed through said second hole in a plurality of different angular positions with respect to said plate portion.

9. The bone plate assembly of claim 8, further comprising:
  a third hole disposed intermediate said first and second holes; and
  another top screw disposed through said third hole, said another top screw extending angularly away from said plane.

10. The bone plate assembly of claim 8, wherein said blade portion includes a hole therein through which said strut screw is threadedly engaged.

11. The bone plate assembly of claim 10, wherein said strut screw includes an intermediate portion between said first hole in said plate portion and said hole in said blade portion capable of engaging bone.

12. The bone plate of claim 8, wherein said bend has a radius defined intermediate said plate portion and said blade portion, said radius dimensioned such that, with said plate portion resting against an outer surface of a bone and said blade portion extending into the bone, said radius fits closely adjacent the outside surface of the bone.

13. The bone plate of claim 12, wherein said radius is about 0.25 inches or less.

* * * * *